(12) United States Patent
Agrawal et al.

(10) Patent No.: US 12,740,796 B2
(45) Date of Patent: Sep. 22, 2026

(54) GRASPER AND REPOSITORY FOR REMOVAL OF MULTIPLE KIDNEY STONE FRAGMENTS

(71) Applicant: C. R. Bard, Inc., Franklin Lakes, NJ (US)

(72) Inventors: Serena R. Agrawal, Salt Lake City, UT (US); Kaitlyn Robinson, Atlanta, GA (US); Hannah Rose Kriscovich, Marietta, GA (US); D. Claire Gloeckner, Lilburn, GA (US); Matthew J. Rothberg, Atlanta, GA (US); Kelsey Leeke, Atlanta, GA (US); Zhihui Yin, Lilburn, GA (US); Nicholas J. Jardine, Holly Springs, NC (US)

(73) Assignee: C. R. Bard, Inc., Franklin Lakes, NJ (US)

( * ) Notice: Subject to any disclaimer, the term of this patent is extended or adjusted under 35 U.S.C. 154(b) by 136 days.

(21) Appl. No.: 18/569,740

(22) PCT Filed: Jun. 16, 2022

(86) PCT No.: PCT/US2022/033882

§ 371 (c)(1),
(2) Date: Dec. 13, 2023

(87) PCT Pub. No.: WO2022/266387

PCT Pub. Date: Dec. 22, 2022

(65) Prior Publication Data

US 2024/0277365 A1 Aug. 22, 2024

Related U.S. Application Data

(60) Provisional application No. 63/211,942, filed on Jun. 17, 2021.

(51) Int. Cl.
*A61B 17/221* (2006.01)
*A61B 1/307* (2006.01)

(52) U.S. Cl.
CPC ............ *A61B 17/221* (2013.01); *A61B 1/307* (2013.01)

(58) Field of Classification Search
CPC ........ A61B 1/018; A61B 1/307; A61B 17/221
See application file for complete search history.

(56) References Cited

U.S. PATENT DOCUMENTS 5,330,484 A * 7/1994 Gunther ............... A61B 17/221 606/127
6,210,370 B1 4/2001 Chi-Sing et al.
(Continued)

FOREIGN PATENT DOCUMENTS

WO 2020139979 A1 7/2020
WO 2022266387 A1 12/2022

OTHER PUBLICATIONS

PCT/US2022/033882 filed Jun. 16, 2022, International Search Report and Written Opinion dated Aug. 19, 2022.

*Primary Examiner* — Mohamed G Gabr
(74) *Attorney, Agent, or Firm* — Rutan & Tucker LLP

(57) ABSTRACT

A medical instrument for insertion into and removal of kidney stone fragments from a urinary tract of a patient body includes a flexible elongate shaft coupled with a fragment retaining mechanism. The retaining mechanism can be configured to retain a plurality of fragments so that the plurality of fragments is removed from the patient with a single insertion/extraction cycle of the instrument. A fragment gathering mechanism urges fragments toward the retaining mechanism. In use, the instrument can be inserted through a working channel of a ureteroscope.

42 Claims, 21 Drawing Sheets

(56) References Cited

U.S. PATENT DOCUMENTS

| | | | | |
|---|---|---|---|---|
| 2004/0153095 | A1 | 8/2004 | Seddon | |
| 2005/0059981 | A1 | 3/2005 | Poll | |
| 2005/0159770 | A1* | 7/2005 | Divani | A61M 29/00 606/200 |
| 2005/0261705 | A1 | 11/2005 | Gist | |
| 2008/0228209 | A1* | 9/2008 | DeMello | A61B 17/32056 606/159 |
| 2011/0106135 | A1* | 5/2011 | Thompson | A61F 2/0105 606/200 |
| 2012/0239064 | A1* | 9/2012 | Cartier | A61B 17/320758 606/159 |
| 2013/0317589 | A1* | 11/2013 | Martin | A61F 2/95 623/1.2 |
| 2018/0235644 | A1* | 8/2018 | Jaffe | A61B 17/221 |

* cited by examiner 40
40
40
214
218
255
267
210
211
260
213
217
250
265
205
206
2B
207
208
205
216
206
A
S
215
212
206A
206B

C
E
300
250
317
310
318
313
315
260
355
311A,311B

C
E
300
250
318
314
314B
315
260
40
311B
255

C
E
300
250
317
311A
313
40
311B
315
260
255

C
E
300
250
317
313
311A, 311B
40
315
260
255

40
414
418
411A
411C
413
417
411B
4C
410
250
405
4B
416
419
E
C
415
412
406
306A
406A
406B
408
407
411B
406A
406B
411A 40
511C
511B
514
518
260
511C
517
513
5C
511B
511A
250
505
5B
521
516
519
515

508A
506B 511B
506A
508
508
507
505

506A
506B 650
660
662
661
40
655

650
607

662
661
40
664
650

662
661
40
650

755
768
767
769
760

705
750
707
706
712
715

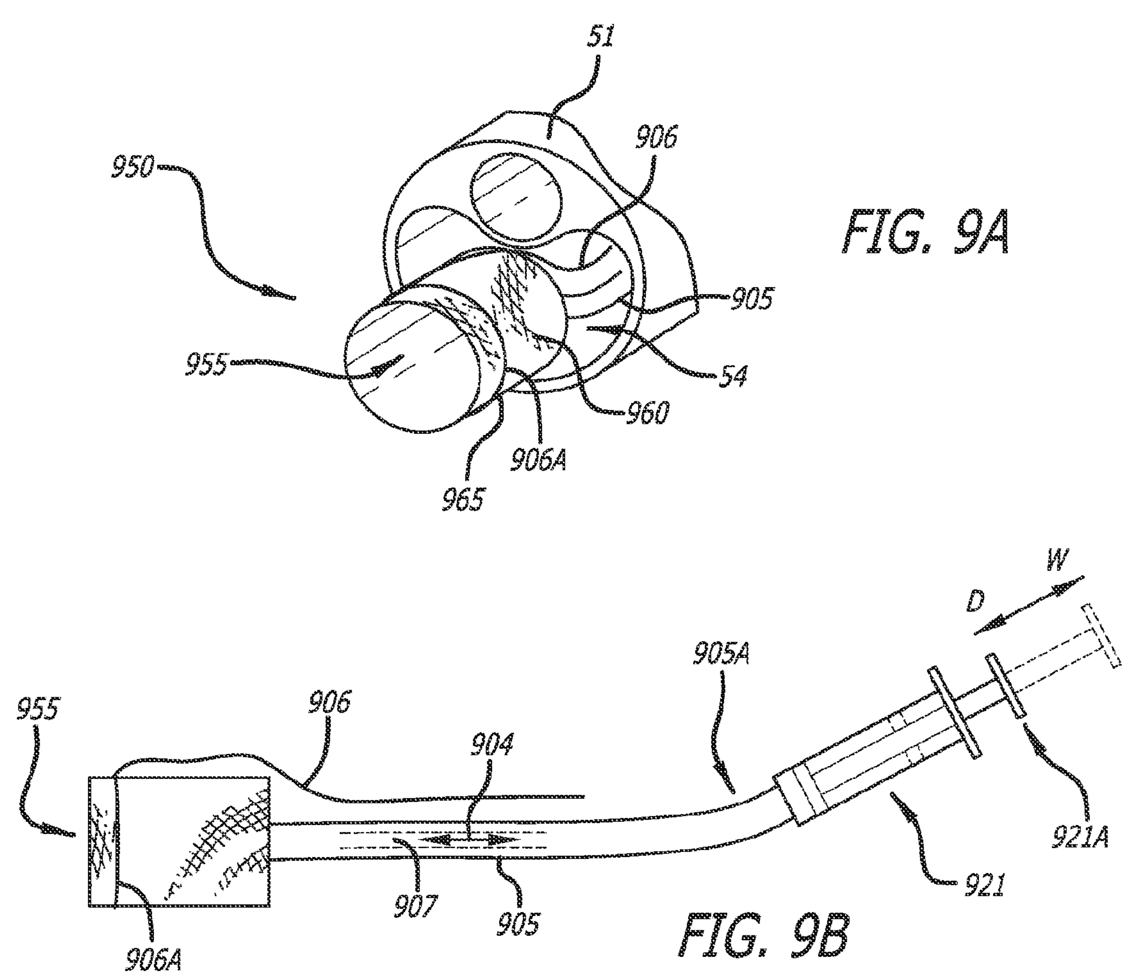
FIG. 9A
FIG. 9B
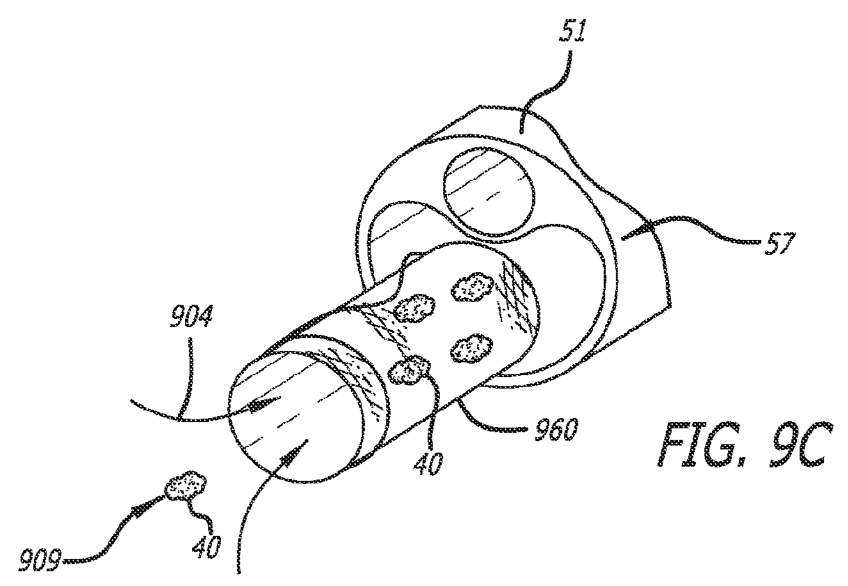
FIG. 9C 51
950

40
960
904A
970
51

950
40
40
904A
970
960
950
40
906

30
970
960
905

905
906
990
965A
967
960A
955

GRASPER AND REPOSITORY FOR REMOVAL OF MULTIPLE KIDNEY STONE FRAGMENTS

PRIORITY

This application is a U.S. national stage application of International Application No. PCT/US2022/033882, filed Jun. 16, 2022, which claims the benefit of priority to U.S. Provisional Application No. 63/211,942, filed Jun. 17, 2021, each of which is incorporated by reference in its entirety into this application.

BACKGROUND

Kidney stones may be treated in various ways. Small kidney stones or fragments may pass through the urinary tract without treatment. Larger kidney stones or kidney stones that block the urinary tract may need to be removed via a medical procedure. Laser lithotripsy is a procedure for removing a kidney stone from the urinary tract of the patient. Laser lithotripsy includes inserting a fiber optic laser through the urinary tract to the calculus. The laser is then activated to break the stone into small fragments that can be passed naturally by the patient or removed via a retrieval instrument. A typical procedure includes inserting a ureteroscope through the urethra, bladder, ureter and if necessary, into the kidney so that a distal tip of the scope is positioned adjacent the stone providing visibility thereof. The fiber optic laser is inserted through a working channel of the ureteroscope to the stone. The laser is then activated to break up the calculus into fragments small enough to be retrieved via a retrieval device such as a basket device or to be passed naturally by the patient through the urinary tract.

In typical cases, many fragments may need to be removed via retrieval device. Current retrieval devices are only capable of removing one or only a few fragments at a time, i.e., with a single insertion/retraction cycle of the device. In some instances, retraction of the retrieval device containing fragments may require retraction of the ureteroscope from the patient. In short, the removal of multiple fragments often requires many insertion/retraction cycles of the retrieval device and/or the ureteroscope causing significant extension of procedure time and exposing the patient to greater risk.

Accordingly, disclosed herein are kidney-stone fragment retrieval devices and methods that enhance the fragment retrieval process by reducing the number of insertion/retraction cycles of the retrieval device during a kidney stone removal procedure.

SUMMARY OF THE INVENTION

Briefly summarized, disclosed herein is a medical instrument for removing kidney stone fragments from a urinary tract of a patient body. The instrument includes a flexible elongate shaft defining a proximal end and a distal end, and the shaft is configured for insertion within the urinary tract. The instrument further includes a fragment retaining mechanism coupled with the shaft at the distal end, and the retaining mechanism is configured to retain a plurality of fragments.

The instrument may be configured for insertion through a working channel of a ureteroscope. As such, the retaining mechanism may be collapsible to accommodate advancement through the working channel. The retaining mechanism is configured to couple with the fragments so that proximal displacement of the retaining mechanism causes proximal displacement of the fragments therewith.

The retaining mechanism may be configured to sequentially receive two or more fragments. The retaining mechanism may also be configured to attach to the plurality of fragments and the attachment may be facilitated by an adhesive applied to the retaining mechanism. In some embodiments, the adhesive includes a hydrogel.

In some embodiments, the retaining mechanism is configured to be inserted through an opening extending through a stone fragment or multiple fragments each having a hole formed therein. In other embodiments, the retaining mechanism includes a container configured to enclose the plurality of fragments. The container may include a flexible wall and the wall may be impervious to fluid. In some embodiments, the container includes a tubular shape within which the fragments may be linearly arranged.

The container may include an entryway for the fragments to enter the container, and the entryway may be configured for selective disposition between an open state allowing passage of fragments therethrough and a closed state inhibiting passage of fragments therethrough. In some embodiments, the entryway is biased toward the closed state and in some embodiments, the entryway is configured for one-way passage of fragments into the container. The container may include a first compartment and a second compartment, and in use, the fragments enter the first compartment and thereafter, the fragments may be subsequently displaced from the first compartment into the second compartment.

The container may include a chemical substance configured to dissolve the fragments, and in some embodiments, the substance may cause the container to dissolve.

The retaining mechanism may be a basket composed of wire elements, and a diameter of the wire elements may be between one to three French, inclusive. The wire elements may be coated with an adhesive so that in use, fragments are attached to the wire elements via the adhesive. In some embodiments, the shaft is coated with the adhesive, so that in use, fragments are attached to the shaft.

In use, a portion of the container may be disposed within the working channel of the ureteroscope. The shaft may include a lumen extending between the proximal end the distal end, and in some embodiments, a portion of the retaining mechanism may be disposed within the lumen during use. In a similar fashion, one or more fragments may be disposed within the working channel of the ureteroscope.

In an embodiment, the retaining mechanism includes an auger extending along at least a portion of the working channel, and the auger is configured to proximally displace the fragments proximally along the working channel via rotation of the auger. A rotating actuator may be coupled with the auger via a elongate member extending along the shaft. In use, activation of the rotating actuator causes proximal displacement of fragments along the working channel.

In some embodiments, shaft includes a lumen is in fluid communication with the container, and the entryway is configured for disposition between the open state and the closed state in accordance with proximal fluid flow and distal fluid flow through the lumen, respectively. Similarly, proximal fluid flow through the lumen may draw fragments toward the entryway. Proximal fluid flow may also draw fragments through the entryway into the container.

In some embodiments, the container is operatively coupled with an elongate member extending along the shaft, and longitudinal displacement of the elongate member with respect to the shaft selectively transitions the entryway between the open state and the closed state. In such an embodiment, the elongate member may define a drawstring extending along a circumference of the container at the entryway, so that distal displacement of the elongate member with respect to the shaft cinches the circumference to transition the entryway toward the closed state.

The retaining mechanism may be coupled with a distal tip of the ureteroscope so that upon articulation of the distal tip, the retaining mechanism articulates therewith.

The instrument may further include a fragment gathering mechanism coupled with the shaft at the distal end, and the gathering mechanism may be configured to urge fragments toward the retaining mechanism. In use, the gathering mechanism may extend distally beyond the retaining mechanism.

The gathering mechanism may be selectively transitionable between a gathering configuration and a non-gathering configuration. When the gathering mechanism is disposed in gathering configuration, proximal displacement of one or more fragments together with the gathering mechanism is constrained, and when the gathering mechanism is disposed in the non-gathering configuration, relative displacement of the gathering mechanism with respect to the fragments is allowed.

In some embodiments, the gathering mechanism includes an elongate hook member extending along the shaft, and the elongate hook member includes a hook at a distal end thereof. The hook is transitionable between a curved shape defining the gathering configuration and a straight shape defining the non-gathering configuration. In some embodiments, manipulation of the elongate hook member at the proximal end of the shaft causes the hook to transition between the straight shape and the curved shape.

In some embodiments, the gathering mechanism includes two or more hooks coupled with two or more elongate hook members extending along the shaft. In such an embodiment, the hooks are positioned adjacent one another in the contracted arrangement defining the non-gathering configuration, and the hooks spaced away from one another in an expanded arrangement defining the gathering configuration. The hooks may also be selectively disposed between the non-gathering configuration and the gathering configuration via manipulation of the elongate hook members at the proximal end of the shaft.

In some embodiments, the gathering mechanism includes a central post having a drill bit at a distal end and the drill bit is configured to form a hole extending through a fragment via rotation of the drill bit. A rotating actuator coupled to the shaft at the proximal end is operatively coupled with the rotating actuator via a first elongate gathering member extending along the shaft. The gathering mechanism further includes two or more arms coupled with the central post. The arms extend radially outward from the central post to define the gathering configuration, and the arms extend along (i.e., parallel to) the central post to define the non-gathering configuration.

The arms are also coupled with a second elongate gathering member extending along the shaft, so that the arms are selectively transitionable between the non-gathering configuration and the gathering configuration via relative longitudinal displacement between the second elongate gathering member and the first elongate gathering member. In use, the gathering mechanism is inserted through a drilled hole in the fragment with the arms in the non-gathering configuration to thread the fragment onto the central post, and the arms are transitioned to the gathering configuration after insertion through the hole to prevent separation of the fragment from the central post.

In some embodiments, the gathering mechanism includes an inflatable balloon coupled with a second elongate gathering member extending along the shaft and the second elongate gathering member includes a fluid lumen extending along its length. The fluid lumen defines fluid communication between the balloon and a fluid device at the proximal end of the shaft, so that the balloon may be selectively inflated defining the gathering configuration and deflated defining the non-gathering configuration. In use the drill bit is rotated to form a hole extending through a fragment, and the gathering mechanism including the balloon is inserted through the hole with the balloon in the deflated state. Thereafter, the balloon in inflated to the gathering configuration to prevent separation of the fragment from the central post.

Further disclosed herein is a method of removing a kidney stone fragments from a urinary tract. The method includes inserting a ureteroscope within the urinary tract and inserting a fragment retrieval instrument through a working channel of the ureteroscope, where the instrument includes a fragment retaining mechanism coupled with a flexible instrument shaft extending along the working channel. The method further includes coupling the retaining mechanism with a plurality of stone fragments without withdrawing the instrument from the urinary tract and withdrawing the instrument from the urinary tract together with the plurality of stone fragments.

The retaining mechanism may include a container, and the step of coupling the retaining mechanism with a plurality of stone fragments includes receiving the fragments through an entryway into the container. The entryway may be configured for disposition between an open state and a closed state, and the method may further include opening the entryway to receive a first fragment, closing the entryway after receiving the first fragment, and subsequently opening the entryway to receive a second fragment after the entryway has been closed.

The container may include a first compartment and a second compartment, the method may further include displacing a fragment from the first compartment to the second compartment.

The method may further include dispensing a chemical substance within the container, where the substance is configured to at least partially dissolve the contained fragments within a surrounding liquid. The method may further include observing a size of the fragments within the container via an imaging system, comparing the observed size with a predefined size limit, and withdrawing the instrument from the urinary tract together with the plurality of stone fragments only after the observed size of the fragments is less than the size limit.

In some embodiments of the method, the instrument further includes a fragment gathering mechanism coupled with the shaft at a distal end of the shaft, and the gathering mechanism is transitionable between a non-gathering configuration and a gathering configuration. In such an embodiment, the method further includes distally displacing the gathering mechanism beyond a fragment in the non-gathering configuration, transitioning the gathering mechanism from the non-gathering configuration to the gathering configuration, and proximally displacing the gathering mechanism together with the fragment toward the retaining mechanism. The method may further include proximally displacing the gathering mechanism together with the fragment into the container.

These and other features of the concepts provided herein will become more apparent to those of skill in the art in view of the accompanying drawings and following description, which describe particular embodiments of such concepts in greater detail.

BRIEF DESCRIPTION OF DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which:

FIG. 9A illustrates a perspective view of a fifth embodiment of a retaining mechanism of FIG. 2A, in accordance with some embodiments;

FIG. 9B illustrates a side view of the retaining mechanism of FIG. 9A, in accordance with some embodiments;

FIGS. 9C-9H illustrate the retaining mechanism of FIGS. 9A-9B in various states of a fragment retrieval process, in accordance with some embodiments;

DETAILED DESCRIPTION

Figures 1A, 1B:
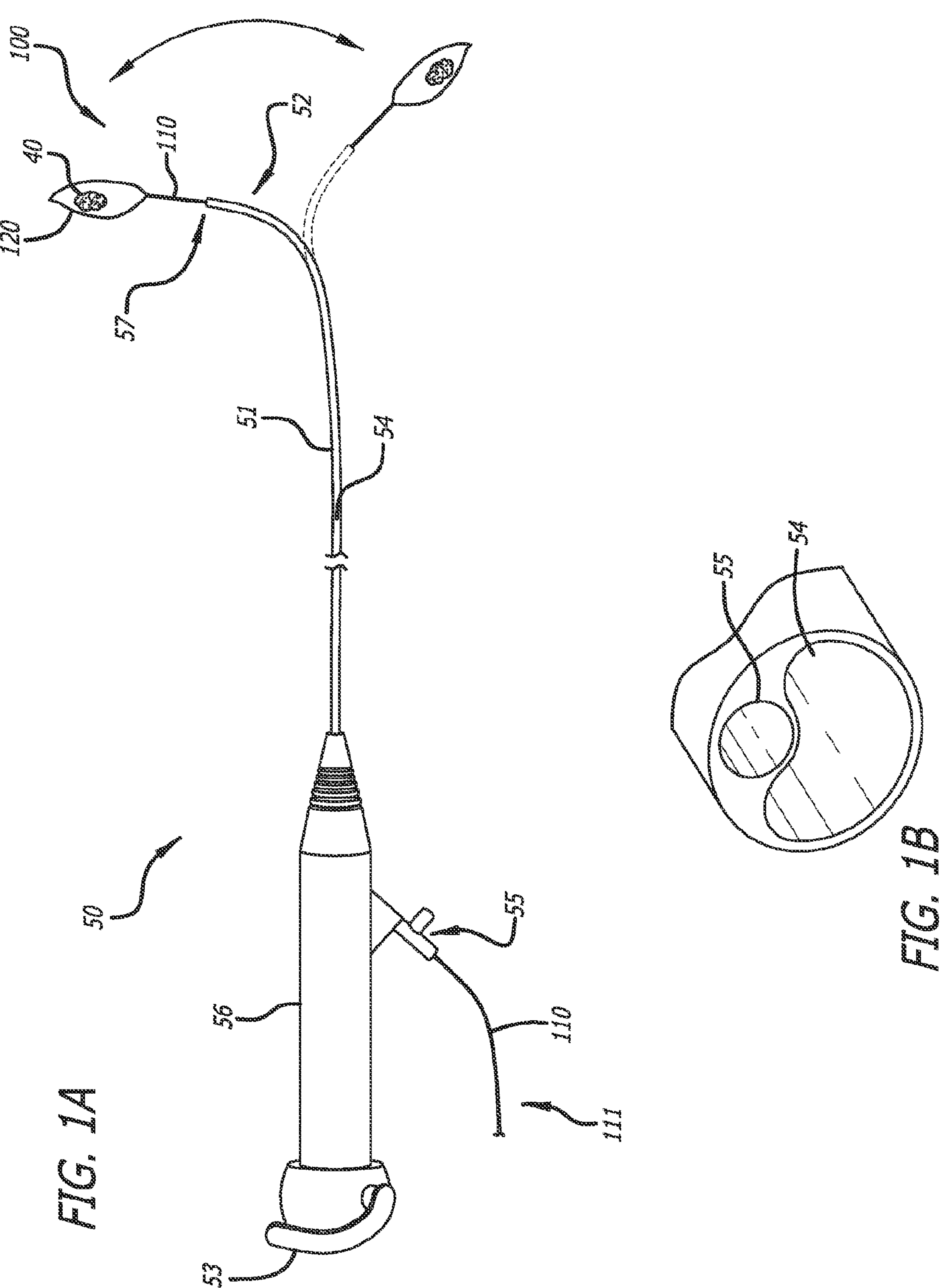
FIG. 1A illustrates a current embodiment of a ureteroscope system combined with a current embodiment of a retrieval instrument.
FIG. 1B is a perspective end view of the ureteroscope shaft of FIG. 1A.

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," "upward," "downward," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise. Also, the words "including," "has," and "having," as used herein, including the claims, shall have the same meaning as the word "comprising."

The terms "or" and "and/or" as used herein are to be interpreted as inclusive or meaning any one or any combination. As an example, "A, B or C" or "A, B and/or C" mean "any of the following: A; B; C; A and B; A and C; B and C; A, B and C." An exception to this definition will occur only when a combination of elements, components, functions, steps or acts are in some way inherently mutually exclusive.

The directional terms "proximal" and "distal" are used herein to refer to opposite locations on a medical device. The proximal end of the device is defined as the end of the device closest to the end-user when the device is in use by the end-user. The distal end is the end opposite the proximal end, along the longitudinal direction of the device, or the end furthest from the end-user.

Unless defined otherwise, all technical and scientific terms used herein have the same meaning as commonly understood by those of ordinary skill in the art.

Any methods disclosed herein include one or more steps or actions for performing the described method. The method steps and/or actions may be interchanged with one another. In other words, unless a specific order of steps or actions is required for proper operation of the embodiment, the order and/or use of specific steps and/or actions may be modified. Moreover, sub-routines or only a portion of a method described herein may be a separate method within the scope of this disclosure. Stated otherwise, some methods may include only a portion of the steps described in a more detailed method.

FIG. 1A illustrates a current embodiment of a ureteroscope 50 coupled with a retrieval instrument 100, and FIG. 1B illustrates a distal end view of a shaft 51 of the ureteroscope 50. The ureteroscope 50 includes a flexible elongate shaft 51 configured for advancement through a urinary tract of a patient body. An articulating portion 52, disposed at a distal end 57 of the shaft 51, is articulated via an articulation lever 53 disposed on a handle 56. The shaft 51 includes a working channel 54 and an image lumen 55 including imaging components (not shown). A flexible elongate instrument shaft 110 is inserted through a working channel 54 of the ureteroscope 50. The working channel 54 extends between an access port 55 and the distal end 57. A basket 120 is coupled to the instrument shaft 110 as a distal end. The basket 120 may be collapsible for disposition within the working channel 54.

In use, the ureteroscope 50 is inserted into the urinary tract to a kidney stone location. A laser lithotripsy device (not shown) is then inserted through the working channel 54 so that a laser beam projecting from the distal end 57 may fragment a kidney stone (or a kidney stone fragment) 40. After fragmentation, the laser device is proximally extracted from the working channel 54 and the retrieval instrument 100 is distally inserted through the working channel 54 from the access port 55 to the distal end 57.

In further use, the instrument shaft 110 may be longitudinally displaced fore and aft along the ureteroscope shaft 50 so that the basket 120 may be extended and retracted with respect to the distal end 57. The basket 120 is generally configured to receive and retain a kidney stone fragment 40. The distal end 57 may be articulated to position the basket 120 adjacent a fragment 40. The stone fragment 40 is received within the basket 120 after which the instrument 100 is removed from the urinary tract so that the fragment 40 may be removed from the basket 120. In some cases, the instrument 100 is removed from working channel 54 while the ureteroscope 50 remains inserted within the urinary tract. The instrument 100 may then be reinserted into the urinary tract so that another fragment 40 may be received into the basket 120 and removed from the patient.

Figures 2A, 2B:
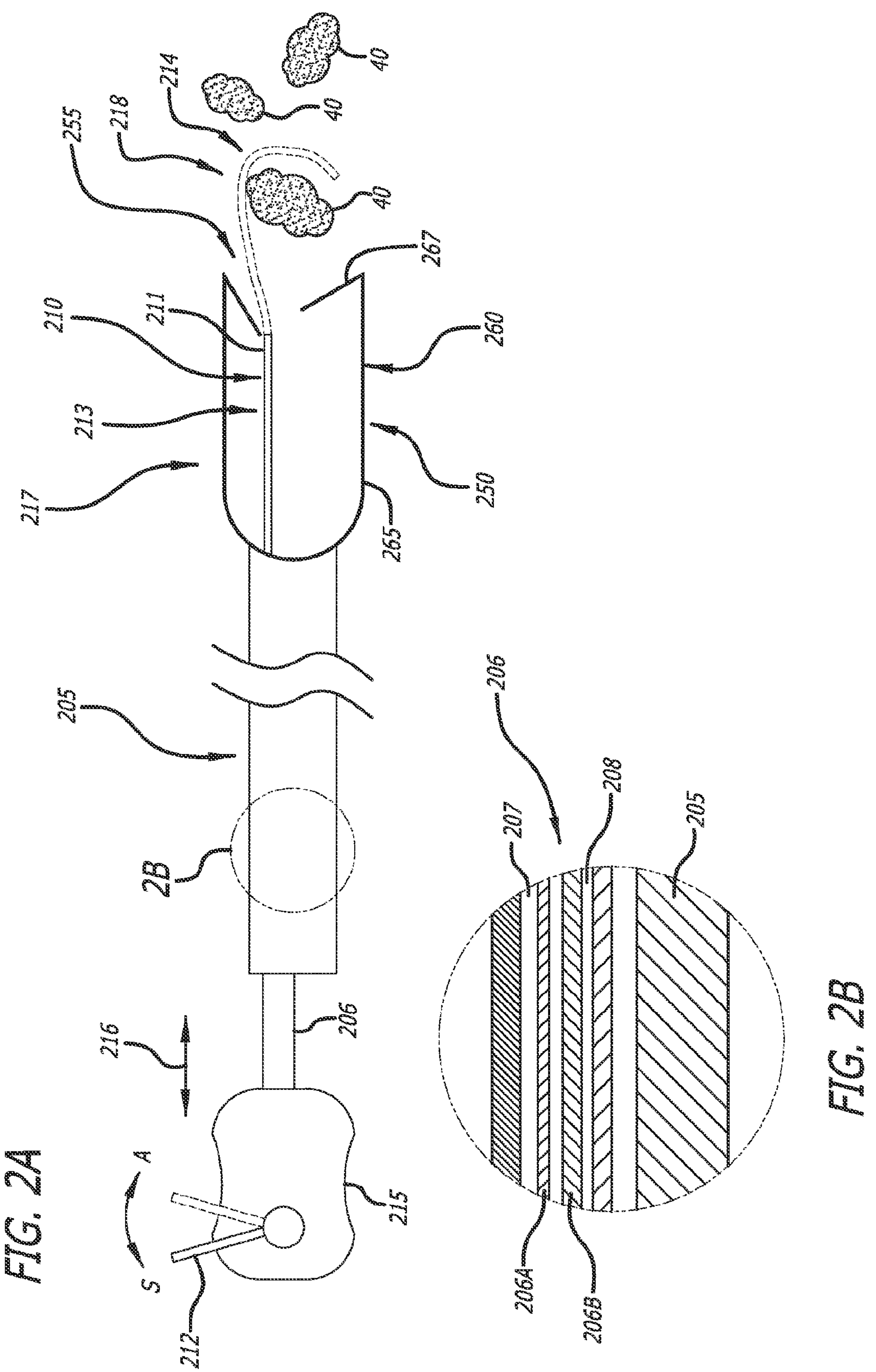
FIG. 2A illustrates a side view of an improved retrieval instrument, in accordance with some embodiments.
FIG. 2B is a detailed cross-sectional view of the instrument shaft of FIG. 2A, in accordance with some embodiments.

FIG. 2A illustrates a first embodiment of an improved fragment retrieval instrument 200 for employment with the ureteroscope 50 of FIGS. 1A-1B. Although not shown in FIG. 2A and other figures that follow, reference to the ureteroscope 50 and components thereof as shown in FIGS. 1A-1B is made in the description hereafter. The instrument 200 may generally include a gathering mechanism 210 and a retaining mechanism 250. The gathering mechanism 210 and the retaining mechanism 250 may be coupled with a flexible elongate instrument shaft 205 configured to extend along the working channel 54. The gathering mechanism 210 and the retaining mechanism 250 may be configured for insertion through the working channel 54. In some embodiments, the gathering mechanism 210 and/or the retaining mechanism 250 may transition between a collapsed state for disposition within the working channel 54 and an expanded state in accordance with operation outside of the working channel 54. Generally speaking, the gathering mechanism 210 may facilitate the displacement of multiple kidney stone fragments 40 toward the retaining mechanism 250, and the retaining mechanism 250 may facilitate retention and removal of multiple gathered stone fragments 40 from the patient. However, in some embodiments, the gathering mechanism 210 may include functionalities associated with retaining fragments 40, and the retaining mechanism 250 may include functionalities associated with gathering fragments 40. As such, in some embodiments, either one of the gathering mechanism 210 or the retaining mechanism 250 may be omitted from the instrument 200.

The shaft 205 may be operatively coupled with either or both of the gathering mechanism 210 or the retaining mechanism 250. The shaft 205 may include one or more elongate components 206 (e.g., wires) extending along the shaft 205. In some embodiments, the elongate components 206 may be disposed in one or more lumens 207 extending along the shaft 205. In the illustrated embodiment, the shaft 205 is attached to the retaining mechanism 250 so that the distal and proximal displacement of the shaft 205 within the working channel 54 causes extension and retraction of the retaining mechanism 250, respectively with respect to the distal end 57. The elongate components 206 may facilitate operation of the gathering mechanism 210 or the retaining mechanism 250 from the proximal end of the shaft 205 by an operator.

In the illustrated embodiment, the retaining mechanism 250 may generally include a container 260 with an entryway 255 (i.e., an opening) for fragments 40 to enter the container 260. The container 260 may be sized to contain a plurality of stone fragments 40. The container 260 may be formed of a basket or a bag. The container 260 may include a flexible or semi-flexible wall 265 which may, in some embodiments, define a tubular shape to accommodate disposition of fragments 40 therein aligned in a linear end-to-end arrangement. In some embodiments, the wall 265 may be impervious to fluid, and in other embodiments, the wall 265 may be pervious to fluid. Still in other embodiments, the wall 265 may define a porosity configured for allowing passage therethrough of stone fragments 40 below a defined size limit. The container 260 may be formed of a plastic material such as polyethylene, polyvinylchloride, silicone, or any other suitable medical grade polymeric material. The container 260 may be configured for disposition between a collapsed configuration (not shown) suitable for insertion through the working channel 54 and an expanded configured for operation outside of the working channel 54.

The entryway 255 may transition between an open configuration and a closed configuration. In the open configuration, passage of fragments 40 through the entryway 255 is allowed, and in the closed configuration, passage of fragments 40 through the entryway 255 is inhibited. In the illustrated embodiment, the entryway 255 may be biased toward the closed configuration. In some embodiments, the entryway 255 may be configured for one-way operation, as such the entryway 255 may allow entry of fragments 40 and prevent the exit of fragments 40.

The container 260 may include one or more gate members 267 which may be coupled to the container wall 265 so as to extend inward from the container wall 265. The gate members 267 may be deflectable or pivotable with respect the container wall 265 so that displacement of the gate members 267 toward each other defines the closed configuration of the entryway 255 and displacement of the gate members 267 away from each other defines the open configuration of the entryway 255. In some embodiments, the gate members 267 may be biased toward each other. In use, the gate members 267 may be opened via contact with the gather mechanism 210.

In some embodiments, the gate members 267 may extend distally into the container 260 at the entryway 255 so that a proximally directed fluid force on the gate members 267 causes the gate members 267 to separate from each other and transition the entryway 255 toward the open configuration. In similar fashion, a distally directed fluid force on the gate members 267 may cause the gate members 267 to displace toward each other and transition the entryway 255 toward the closed configuration. In some embodiments, the container 260 (or more specifically, the wall 265 and/or one or more of the gate members 267) may include an opening (not shown) through which the gathering mechanism 210 or a portion thereof may extend during use.

The gathering mechanism 210 may transition between a gathering configuration and a non-gathering configuration. In the illustrated embodiment, the gathering mechanism 210 includes an elongate articulating member 211 configured to transition between a straight shape 213 defining the non-gathering configuration and a curved shape 214 (i.e., a hook shape) defining the gathering configuration. The articulating elongate member 211 may be coupled with an articulation actuator 212 so that manipulation of the actuator 212 transitions the articulating member 211 between the straight shape 213 and the curved shape 214. By way of example, the articulating member 211 may be disposed in the straight shape 213 when the actuator 212 is displaced to the straight "S" position, and the articulating member 211 may be disposed in the curved shape 213 when the actuator 212 is displaced to the articulate "A" position. The gathering mechanism 210 is also longitudinally displaceable relative to the retaining mechanism 250 between a retracted position 217 and an extended position 218 via proximal and distal displacement of a handle 215 as indicated by the arrow 216. In some embodiments, the handle 215 may include the articulation actuator 212.

In some embodiments, the articulating mechanism 250 may be operatively coupled with the gathering mechanism 210. More specifically, the articulating member 211 may be coupled with the gate members 267. In such an embodiment, transitioning the articulating member 211 from the straight shape 213 to the curved shape 214 may also transition the gate members 267 from a closed state to an open state. Conversely, transitioning the articulating member 211 from the curved shape 214 to the straight shape 213 may transition the gate members 267 from the open state to the closed state.

In an alternative embodiment, the articulating member 211 may define broom structure (not shown) configured to sweep fragments 40 toward the entryway 255 in a gathering configuration and pass distally by fragments 40 in a non-gathering configuration. In the gathering configuration broom bristles may extend perpendicular to the urinary tract and in the non-gathering configuration the broom bristles may extended parallel to the urinary tract.

By way of summary, the operator may displace the articulating member 211 between the retracted position 217 and an extend position 218 via proximal and distal movement of the handle 215. The operator may also transition the articulating member 211 between the straight shape 213 and the curved shape 214 via manipulation of the articulation actuator 212.

FIG. 2B is a detailed cross-section view of the shaft 205, in accordance with some embodiments. As shown, shaft 205 includes a lumen 207 having elongate components 206 extending therethrough. The elongate components 206 include a first gathering shaft 206A and a second gathering shaft 206B extending along the shaft 205. The second gathering shaft 206B is disposed within a lumen 208 of the first gathering shaft 206A. The first gathering shaft 206A couples the articulating member 211 with handle 215 to define longitudinal co-movement of the articulating member 211 and the handle 215. The second gathering shaft 206B operatively couples the articulating member 211 with the articulation actuator 212 so that manipulation of the actuator 212 causes articulation of the articulating member 211.

Figures 2C, 2D, 2E, 2F:
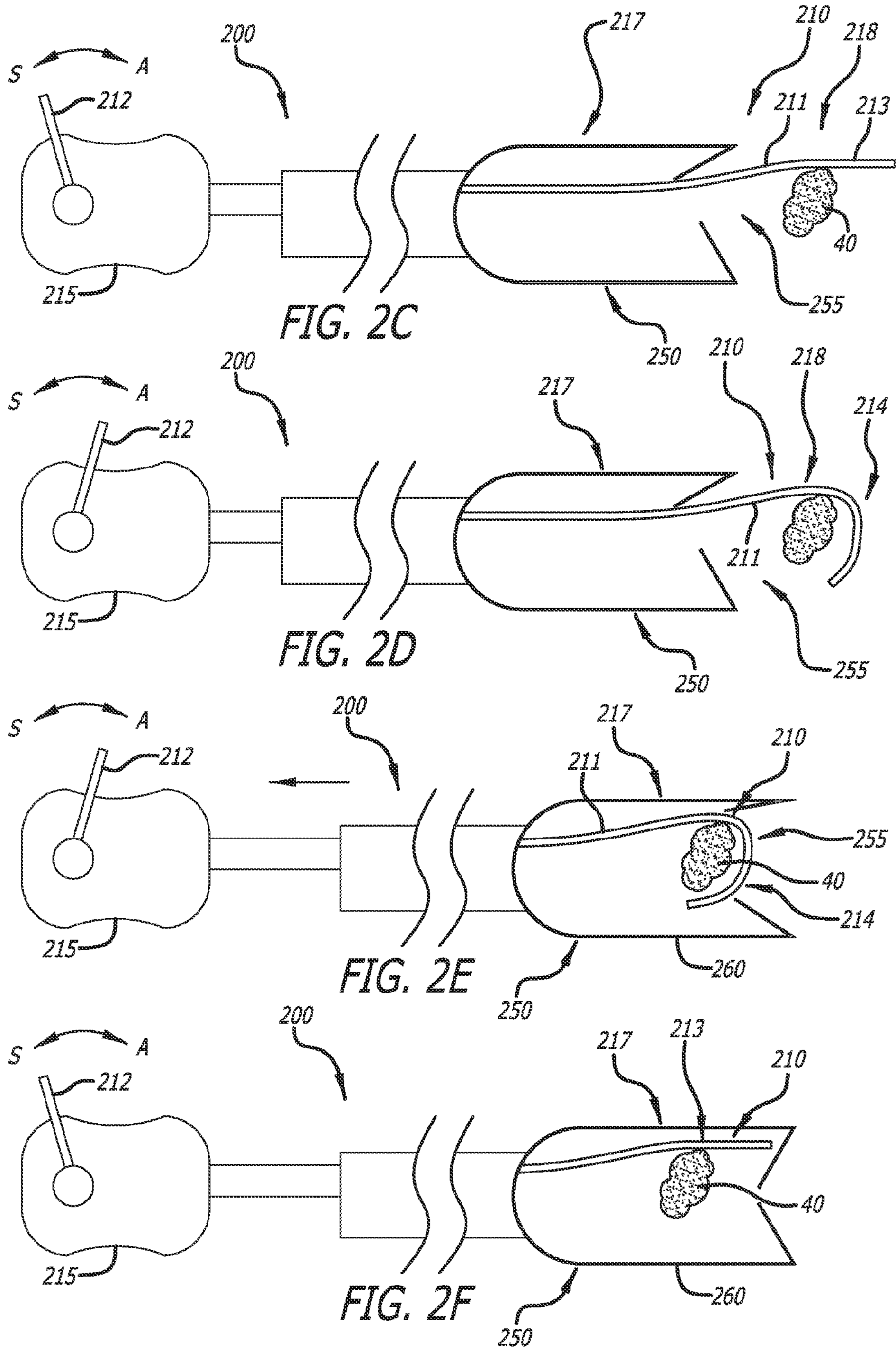
FIGS. 2C-2F illustrate the instrument of FIGS. 2A-2B in various states of a fragment retrieval process, in accordance with some embodiments.

FIGS. 2C-2F illustrate the instrument 200 in various states of a fragment retrieval process. In FIG. 2C, the articulating member 211 is extended from the retracted position 217 of FIG. 2A to the extended position 218 with the articulating member 211 remaining in the straight shape 213 in accordance with the actuator 212 disposed at the "S" position. As shown, the articulating member 211 is positioned laterally adjacent the fragment 40. The handle 215 is distally displaced in relation to the position of the handle 215 shown in FIG. 2A, and the entryway 255 is in the closed configuration.

In FIG. 2D, the articulating member 211 is in the extended position 218. The actuator 212 is displaced to the "A" position to transition the articulating member 211 from the straight shape 213 to the curved shape 214 thereby extending around the fragment 40. The entryway 255 remains in the closed configuration In FIG. 2E, the articulating member 211 remains in the curved shape 214 extending around the fragment 40. The articulating member 211 is retracted from the extended position 218 to the retracted position 217 so that the fragment 40 together with the articulating member 211 is displaced through the entryway 255 into the container 260. During passage of the fragment 40 together with the articulating member 211 through the entryway 255, the entryway 255 transitions from the closed configuration to the open configuration.

In FIG. 2F, the actuator 212 is displaced to the "S" position to transition the articulating member 211 from the curved shape 214 to the straight shape 213 thereby releasing the fragment 40 within the container 260. The entryway 255, as biased, returns to the closed configuration after the fragment 40 is fully within the container 260. The retrieval process of FIGS. 2C-2F is repeated for additional kidney stone fragments 40.

FIGS. 3A-3F illustrate a second embodiment of a retrieval instrument 300 that can, in certain respects, resemble components of the retrieval instrument 200 described in connection with FIGS. 2A-2F. It will be appreciated that all the illustrated embodiments may have analogous features. Accordingly, like features are designated with like reference numerals, with the leading digits increment to "3." For instance, the handle is designated as "215" in FIGS. 2A-2F, and an analogous handle is designated as "315" in FIG. 3A-3F. Relevant disclosure set forth above regarding similarly identified features thus may not be repeated hereafter. Moreover, specific features of the instrument 200 and related components shown in FIGS. 2A-2F may not be shown or identified by a reference numeral in the drawings or specifically discussed in the written description that follows.

However, such features may clearly be the same, or substantially the same, as features depicted in other embodiments and/or described with respect to such embodiments. Accordingly, the relevant descriptions of such features apply equally to the features of the retrieval instrument 300. Any suitable combination of the features, and variations of the same, described with respect to the retrieval instrument 200 combination and components illustrated in FIGS. 2A-2F can be employed with the retrieval instrument 300 and components of FIG. 3A-3F, and vice versa. This pattern of disclosure applies equally to further embodiments depicted in subsequent figures and described hereafter.

Figures 3A, 3B:
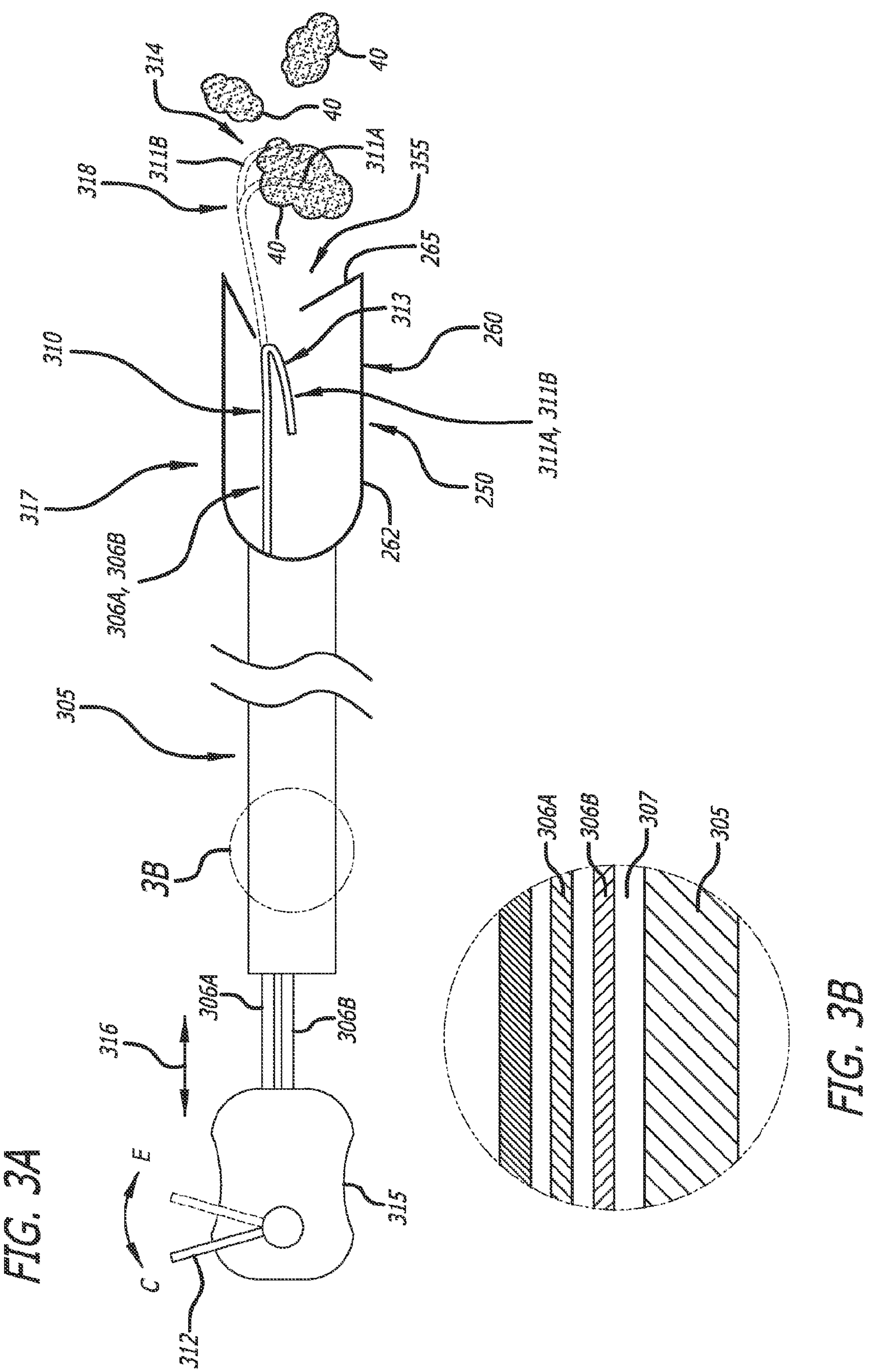
FIG. 3A illustrates a side view of a second embodiment of a retrieval instrument, in accordance with some embodiments.
FIG. 3B is a detailed cross-sectional view of the instrument shaft of FIG. 3A, in accordance with some embodiments.

Referring to FIG. 3A, the instrument 300 may generally include a gathering mechanism 310 and the retaining mechanism 250 of FIGS. 2A-2F. Although not shown in FIG. 3A and other figures that follow, reference to the ureteroscope 50 and components thereof as shown in FIGS. 1A-1B is made in the description below. The gathering mechanism 310 and the retaining mechanism 250 may be coupled with a flexible elongate instrument shaft 305 configured to extend along the working channel 54. The gathering mechanism 310 and a retaining mechanism 250 may be configured for insertion through the working channel 54. In some embodiments, the gathering mechanism 310 and/or the retaining mechanism 250 may transition between a collapsed state for disposition in the working channel 54 and an expanded state in accordance with operation outside of the working channel 54. Generally speaking, the gathering mechanism 310 may facilitate the displacement of a multiple kidney stone fragments 40 toward the retaining mechanism 250, and the retaining mechanism 250 may facilitate retention and removal of multiple gathered stone fragments 40 from the patient.

The shaft 305 may be operatively coupled with either or both of the gathering mechanism 310 or the retaining mechanism 250. The shaft 305 may include one or more elongate components 306 (e.g., wires) extending along the shaft 305. In some embodiments, the elongate components 306 may be disposed in one or more lumens 307 extending along the shaft 305. In the illustrated embodiment, the shaft 305 is attached to the retaining mechanism 250 so that the distal and proximal displacement of the shaft 305 within the working channel 54 causes extension and retraction of the retaining mechanism 250 with respect to the distal end 57. The elongate components 306 may facilitate operation of the gathering mechanism 310 or the retaining mechanism 250 from the proximal end of the shaft 305 by an operator.

The gathering mechanism 310 may transition between a gathering configuration and a non-gathering configuration. In the illustrated embodiment, the gathering mechanism 310 includes two or more hooks, such as hooks 311A, 311B. The hooks 311A, 311B are configured to transition between a collapsed state 313 defining the non-gathering configuration and an expanded state 314 defining the gathering configuration. In the collapsed state 313, the hooks 311A, 311B are positioned adjacent one another, e.g., in a stacked configuration (shown extending into the page in FIG. 3C). In the expanded state 314, the hooks 311A, 311B are rotationally separated from one another defining a separation angle 314A (see FIG. 3D). The separation angel 314A may be between about 10 and 90 degrees, between about 30 and 60 degrees or about 45 degrees. In some embodiments, the hooks 311A, 311B may include a net (not shown) extending between the hooks 311A, 311B in the expanded state. In some embodiments, the hooks 311A, 311B may also transition between a straight shape (see FIG. 2C) in the non-gathering configuration and the curved shape in the gathering configuration.

The hooks 311A, 311B are coupled with an expansion actuator 312 so that manipulation of the actuator 312 transitions the hooks 311A, 311B between the collapsed state 313 and the expanded state 314. By way of example, the hooks 311A, 311B are disposed in the collapsed state 313 when the actuator 312 is displaced toward the collapse "C" position, and the hooks 311A, 311B are disposed in the expanded state 314 when the actuator 312 is displaced toward the expand "E" position. The hooks 311A, 311B are longitudinally displaceable relative to the retaining mechanism 250 between a retracted position 317 and an extended position 318 via proximal and distal displacement of a handle 315 as indicated by the arrow 316.

By way of summary, the operator may displace the handle 315 to displace the hooks 311A, 311B between the retracted position 317 and the extended position 318. The operator may also transition the hooks 311A, 311B between the collapsed state 313 and the expanded state 314 via manipulation of the actuator 312 between the "C" position and the "E" position.

FIG. 3B is a detailed cross-sectional view of the shaft 305, in accordance with some embodiments. As shown, shaft 305 includes a lumen 307 having elongate components 306 extending therethrough. The elongate components 306 include a first hook shaft 306A coupled with the first hook 311A and a second hook shaft 306B coupled with the second hook 311B. The first and second hook shafts 306A, 306B may be configured so that relative rotation of the shafts 306A, 306B causes to the hooks 311A, 311B to rotate toward each other to define the collapsed state 313 and away from each other to define the expanded state 314. The first and second shafts 306A, 306B couple the hooks 311A, 311B with handle 315 to define longitudinal co-movement of the hooks 311A, 311B and the handle 315. One of the first shaft 306A or second shaft 306B may be operatively coupled with the actuator 312 so that manipulation of the actuator 312 rotates the one of the first shaft 306A or second shaft 306B to cause the hooks 311A, 311B to expand and collapse.

Figures 3C, 3D, 3E, 3F:
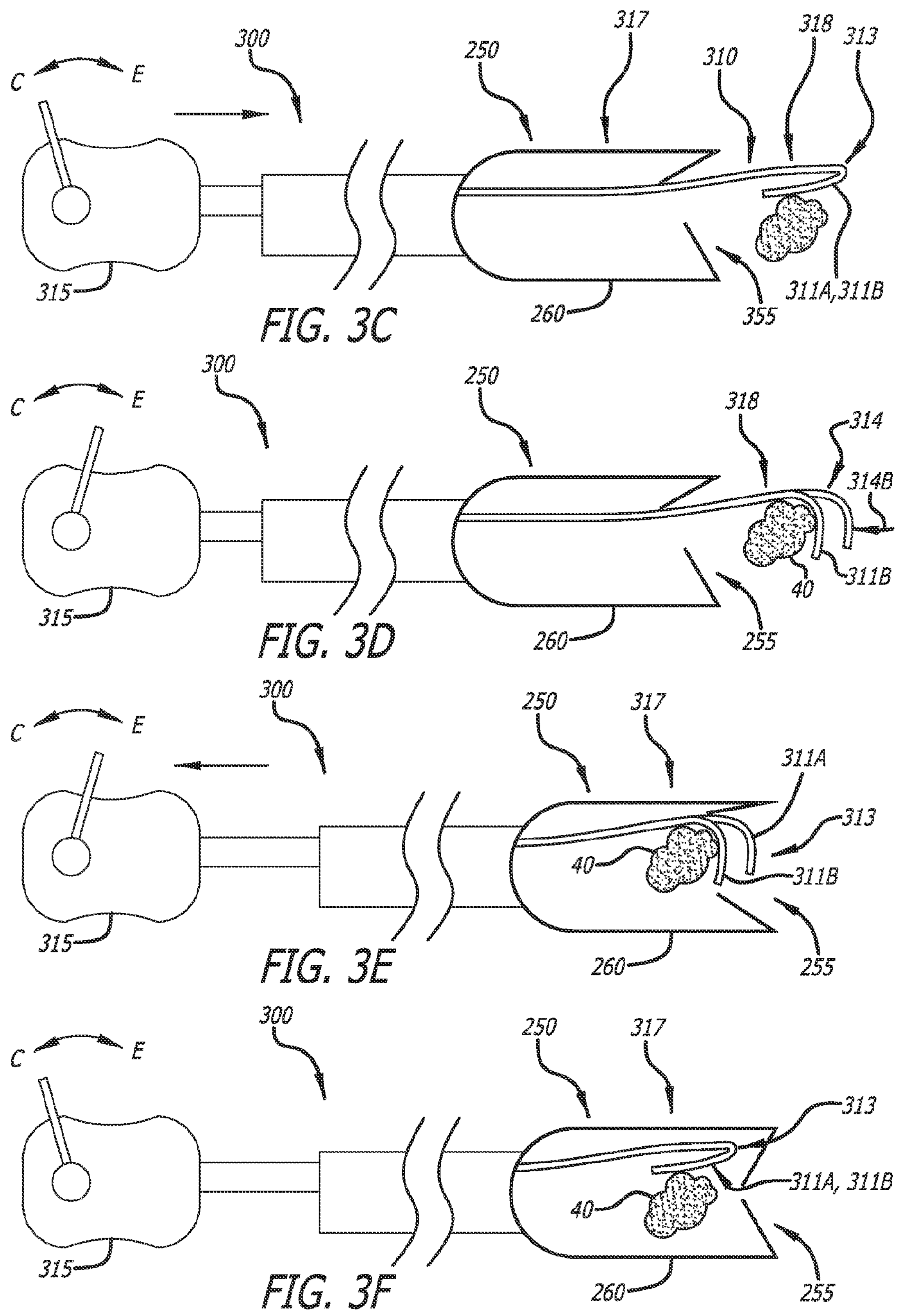
FIGS. 3C-3F illustrate the instrument of FIGS. 3A-3B in various states of a fragment retrieval process, in accordance with some embodiments.

FIGS. 3C-3F illustrate the instrument 300 in various states of a fragment retrieval process. In FIG. 3C, the hooks 311A, 311B are extended from retracted position 317 of FIG. 3A to the extended position 318 with the hooks 311A, 311B remaining in the collapsed state 313. As shown, the hooks 311A, 311B, while in the collapsed state 313, may be positioned laterally adjacent the fragment 40 so that the hooks 311A, 311B may be distally displaced beyond the fragment 40. The articulation handle 315 is distally displaced in relation to the position of the handle 315 shown in FIG. 3A and the entryway 255 is in the closed configuration.

In FIG. 3D, the hooks 311A, 311B are in the extended position 318. The hooks 311A, 311B are transitioned from the collapsed state 313 to the expanded state 314 defining the angle 314A so as to extend around and on each side of the fragment 40. The entryway 255 remains in the closed configuration.

In FIG. 3E, the hooks 311A, 311B remain in the expanded state 314 extending around the fragment 40. The hooks 311A, 311B are retracted from the extended position 318 to the retracted position 317 so that the fragment 40 together with the hooks 311 is displaced through the entryway 255 into the container 260. During passage of the fragment 40 together with the hooks 311 through the entryway 255, the entryway 255 transitions from the closed configuration to the open configuration.

In FIG. 3F, the hooks 311A, 311B are transitioned from the expanded state 314 to the collapsed state 313 thereby releasing the fragment 40 within the container 260. The entryway 255, as biased, is transitioned back to the closed configuration after the fragment 40 is fully disposed within the container 260. The retrieval process of FIGS. 3C-3F may be repeated to gather and retain additional kidney stone fragments 40 within the container 260.

Figures 4A, 4B, 4C:
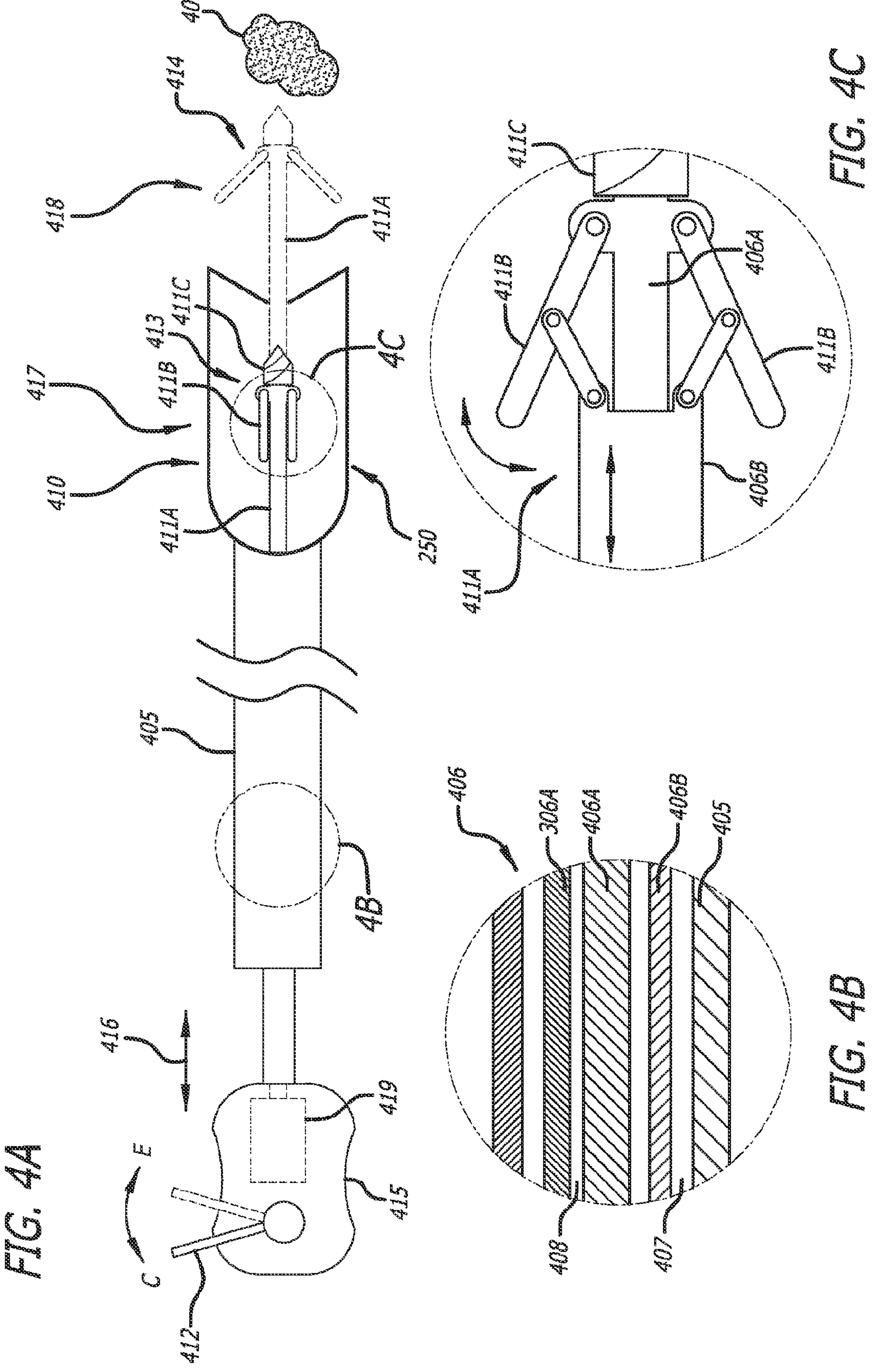
FIG. 4A illustrates a side view of a third embodiment of a retrieval instrument, in accordance with some embodiments.
FIG. 4B is a detailed cross-sectional view of the instrument shaft of FIG. 4A, in accordance with some embodiments.
FIG. 4C is a detailed illustration of the gathering mechanism of FIG. 4A, in accordance with some embodiments.

FIG. 4A illustrates a third embodiment of the instrument 400. Although not shown in FIG. 4A and other figures that follow, reference to the ureteroscope 50 and components thereof as shown in FIGS. 1A-1B is made in the description below. The instrument 400 may generally include a gathering mechanism 410 and the retaining mechanism 250 of FIGS. 2A-2F). The gathering mechanism 410 and the retaining mechanism 250 may be coupled with a flexible elongate instrument shaft 405 configured to extend along the working channel 54. The gathering mechanism 410 and a retaining mechanism 250 may be configured for insertion through the working channel 54. In some embodiments, the gathering mechanism 410 and/or the retaining mechanism 250 may transition between a collapsed state for disposition in the working channel 54 and an expanded state in accordance with operation outside of the working channel 54. Generally speaking, the gathering mechanism 410 may facilitate the displacement of a multiple kidney stone fragments 40 toward the retaining mechanism 250, and the retaining mechanism 250 may facilitate retention and removal of multiple gathered stone fragments 40 from the patient.

The shaft 405 may be operatively coupled with the gathering mechanism 410 and/or the retaining mechanism 250. The shaft 405 may include one or more elongate components 406 (e.g., wires) extending along the shaft 405. In some embodiments, the elongate components 406 may be disposed in one or more lumens 407 extending along the shaft 405. In the illustrated embodiment, the shaft 405 is attached to the retaining mechanism 250 so that the distal and proximal displacement of the shaft 405 within the working channel 54 causes extension and retraction of the retaining mechanism 450 with respect to the distal end 57. The elongate components 406 may facilitate operation of the gathering mechanism 410 or the retaining mechanism 250 from the proximal end of the shaft 405 by an operator.

The gathering mechanism 410 may transition between a gathering configuration and a non-gathering configuration. In the illustrated embodiment, the gathering mechanism 410 includes a central post 411A coupled with two or more expandable arms 411B. The arms 411B are configured to transition between a collapsed state 413 defining the non-gathering configuration and an expanded state 414 defining the gathering configuration. In the collapsed state 413, the arms 411B may be positioned laterally adjacent the post 411A (e.g., parallel to the central post 411A) to define the collapsed state 413. In the expanded state 414, the arms 411 are extended radially outward from the central post 411A, such as in an umbrella-like fashion, for example. In some embodiments, the expandable arms 411B may include one or more of a textured surface, serrated portions, or an adhesive to assist the expandable arms 411B in gripping or attaching to the fragments 40.

The arms 411B are coupled with an expansion actuator 412 so that manipulation of the actuator 412 transitions the arms 411B between the collapsed state 413 and the expanded state 414. By way of example, the arms 411B may be disposed in the collapsed state 413 when the actuator 412 is displaced toward the "C" position as shown, and the arms 411B may be disposed in the expanded state 414 when the actuator 412 is displaced toward the "E" position.

The central post 411A includes a drill bit 411C attached to the distal end of the central post 411A to facilitate forming a hole 41 (see FIG. 4E) extending through the fragment 40 via rotation of the drill bit 411C. The drill bit 411C is coupled with a rotating actuator 419 (e.g., a motor) disposed within the handle 415 so that the drill bit 411C rotates in accordance with activating the rotating actuator 419.

The gathering mechanism 410 is longitudinally displaceable relative to the retaining mechanism 250 between a retracted position 417 and an extended position 418 via proximal and distal displacement of a handle 415 as indicated by the arrow 416. By way of summary, the operator may displace the gathering mechanism 410 between the retracted position 417 and the extended position 418 via displacement of the handle 415. The operator may also transition the arms 411B between the collapsed state 413 and the expanded state 414 via manipulation of the actuator 412.

FIG. 4B is a detailed cross-sectional view of the shaft 405, in accordance with some embodiments. As shown, shaft 405 includes a lumen 407 having elongate components 406 extending therethrough. The elongate components 406 include a central gathering shaft 406A and an annular gathering shaft 406B extending along the shaft 405, the central gathering shaft 406A and an annular gathering shaft 406B defining the central post 411A. The central gathering shaft 406A is disposed within a lumen 408 of the annular gathering shaft 406B. The central gathering shaft 406A couples the gathering mechanism 410 with the handle 415 to define longitudinal co-movement of the gathering mechanism 410 and the handle 415. The annular gathering shaft 406B is operatively coupled with the arms 411B so that distal and proximal displacement of annular gathering shaft 406B relative to the central gathering shaft 406A causes expansion and contraction of the arms 411B.

FIG. 4C is a detailed view of a distal portion of the gathering mechanism 410. In the exemplary illustrated embodiment, the gathering mechanism 410 includes two arms 411B. In other embodiments, the gathering mechanism 410 may include only one arm 411B or more than two arms 411B. A distal end of the arms 411B may be pivotably coupled with the central gathering shaft 406A so that a proximal end of the arms 411B may extend radially away from the central gathering shaft 406A. The arms 411B are operatively coupled with the annular gathering shaft 406B so that relative displacement between the annular gathering shaft 406B and the central gathering shaft 406A causes radial displacement of the proximal ends of the arms 411B.

Figure 4D:
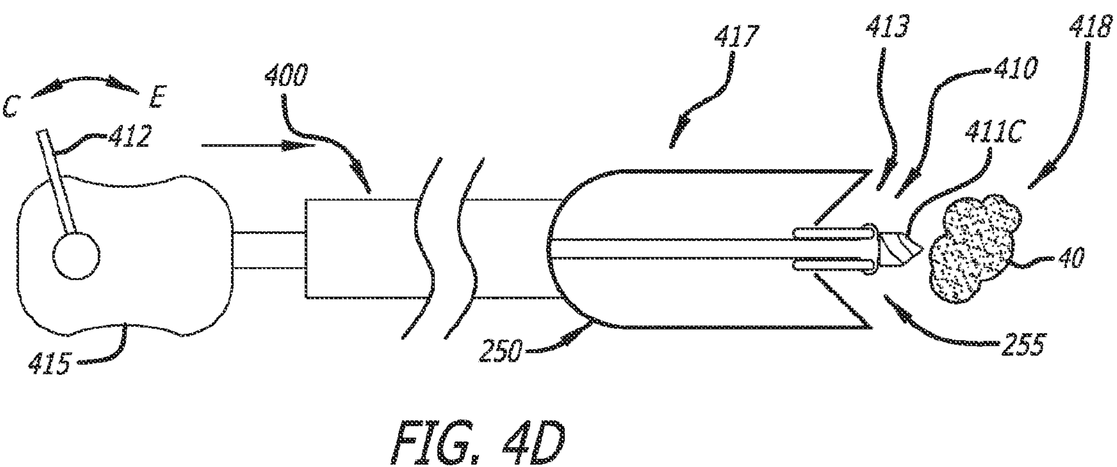
FIGS. 4D-4H illustrate the instrument of FIGS. 4A-4C in various states of a fragment retrieval process, in accordance with some embodiments.

FIGS. 4D-4G illustrate the instrument 400 in various states of a fragment retrieval process. In FIG. 4D, the gathering mechanism 410 is extended distally away from the retracted position 417 toward the extended position 418 with the arms 411B remaining in the collapsed state 413. As shown, the gathering mechanism 410 may be distally displaced to contact the fragment 40 with the drill bit 411C.

Figure 4E:
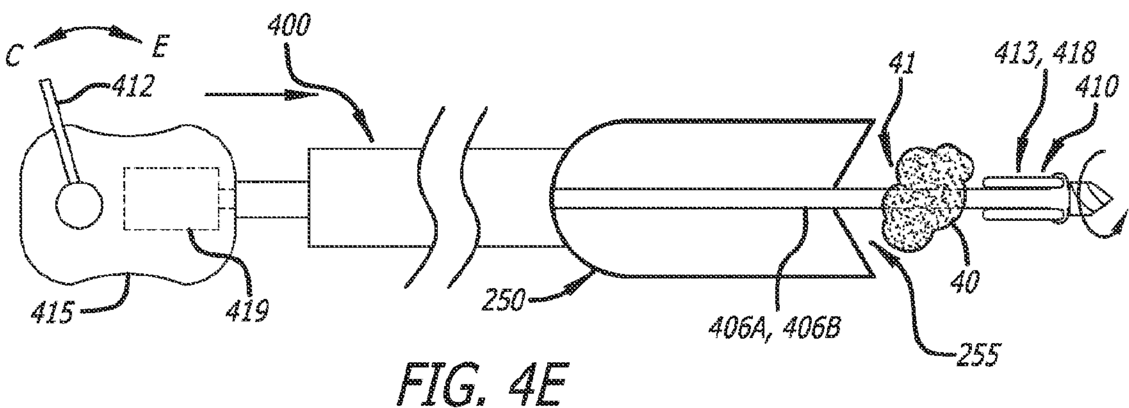

In FIG. 4E, the rotating actuator 419 is energized in combination with further distal displacement of the gathering mechanism 410 to form a hole 41 through the fragment 40. The gathering mechanism 410 is inserted through the hole 41 as the gathering mechanism 410 is further distally displaced to the extended position 418 thereby threading the fragment 40 onto the central post 411A. The handle 415 is also distally displaced in relation to the position of the handle 415 shown in FIG. 4A, and the entryway 255 is in the closed configuration.

Figure 4F:
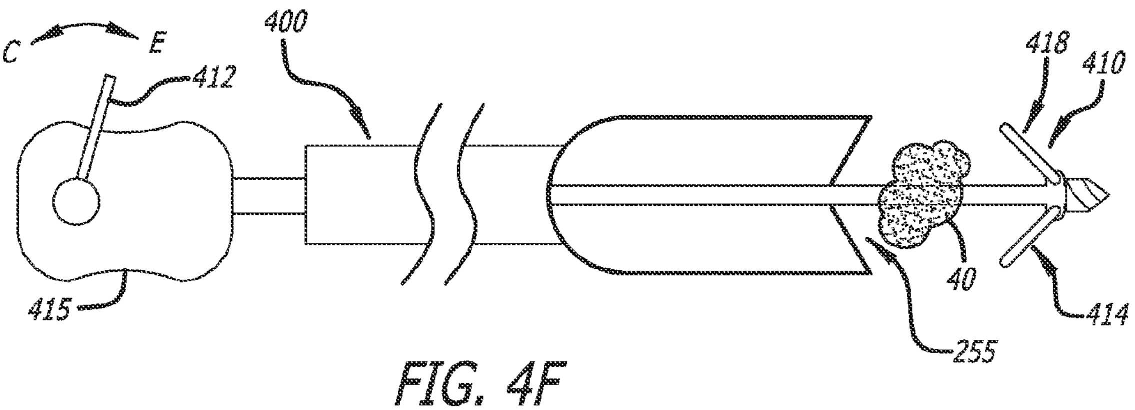

In FIG. 4F, the gathering mechanism 410 is in the extended position 418. The arms 411B are transitioned from the collapsed state 413 to the expanded state 414 so as to extend radially outward beyond a circumference of the hole 41. The entryway 255 remains in the closed configuration.

Figure 4G:
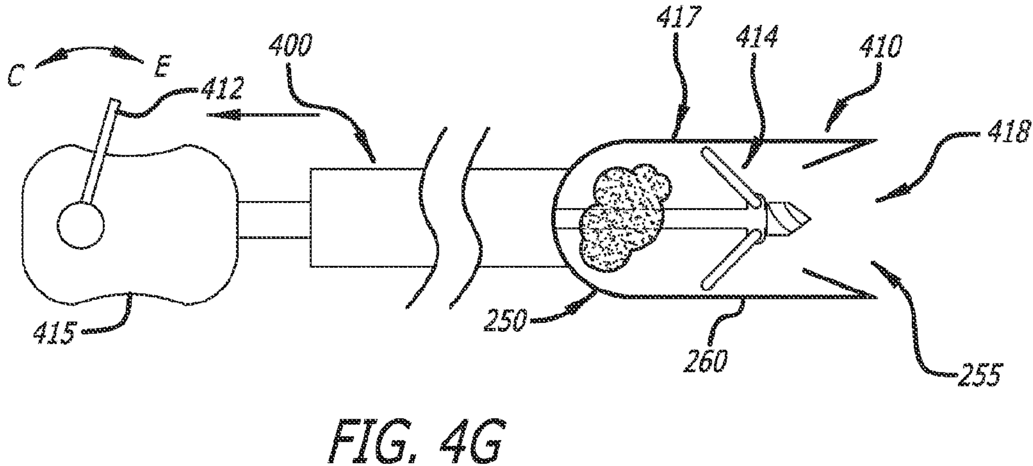

In FIG. 4G, the arms 411B remain in the expanded state 414. The gathering mechanism 410 is retracted from the extended position 418 to the retracted position 417 so that the fragment 40 together with the gathering mechanism 410 is displaced through the entryway 255 into the container 260. During passage of the fragment 40 together with the gathering mechanism 410 through the entryway 255, the entryway 255 transitions from the closed configuration to the open configuration.

Figure 4H:
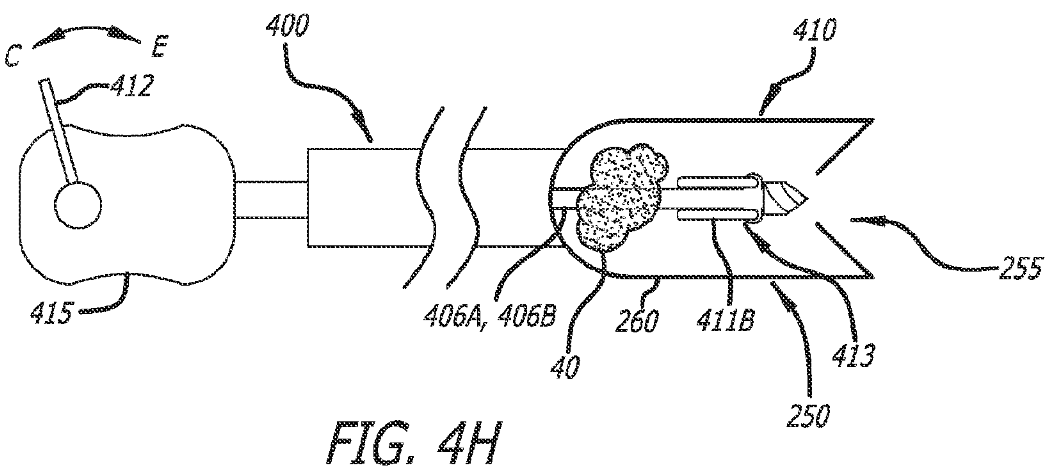

In FIG. 4H, the arms 411B are transitioned from the expanded state 414 to the collapsed state 413. The fragment 40 remains threaded onto the central post 411A. The entryway 255, as biased, returns to the closed configuration after the fragment 40 is fully within the container 260. The retrieval process of FIGS. 4D-4H may be repeated to gather and retain additional kidney stone fragments 40.

In some embodiments, since the fragments 40 are retained on the central post 411A in accordance with the gathering process, the retaining mechanism 250 may be omitted from the instrument 400.

The instrument 500 may generally include a gathering mechanism 510 and the retaining mechanism 250 of FIGS. 2A-2F. Although not shown in FIG. 5A and other figures that follow, reference to the ureteroscope 50 and components thereof as shown in FIGS. 1A-1B is made in the description below. The gathering mechanism 510 and the retaining mechanism 250 may be coupled with a flexible elongate instrument shaft 505 configured to extend along the working channel 54. The gathering mechanism 510 and a retaining mechanism 250 may be configured for insertion through the working channel 54. In some embodiments, the gathering mechanism 510 and/or the retaining mechanism 250 may transition between a collapsed state for disposition within the working channel 54 and an expanded state in accordance with operation outside of the working channel 54. Generally speaking, the gathering mechanism 510 may facilitate the displacement of a multiple kidney stone fragments 40 toward the retaining mechanism 250, and the retaining mechanism 250 may facilitate retention and removal of multiple gathered stone fragments 40 from the patient.

The shaft 505 may be operatively coupled with the gathering mechanism 510 and/or the retaining mechanism 250. The shaft 505 may include one or more elongate components 506 extending along the shaft 505. In some embodiments, the elongate components 506 may be disposed in one or more lumens 507 extending along the shaft 505. In the illustrated embodiment, the shaft 505 is attached to the retaining mechanism 250 so that the distal and proximal displacement of the shaft 505 within the working channel 54 causes extension and retraction of the retaining mechanism 550 with respect to the distal end 57. The elongate components 506 may facilitate operation of the gathering mechanism 510 or the retaining mechanism 250 from the proximal end of the shaft 505 by an operator.

The gathering mechanism 510 may transition between a gathering configuration and a non-gathering configuration. In the illustrated embodiment, the gathering mechanism 510 includes a central post 511A and a balloon 511B. The balloon 511B is configured to transition between a deflated state 513 defining the non-gathering configuration and an inflated state 514 defining the gathering configuration. The balloon 511B may be coupled with a fluid device 521 (e.g., a syringe having a plunger 521A) so that operation/manipulation of the fluid device 512 transitions the balloon 511B between the deflated state 513 and the inflated state 514. In the deflated state 513, the balloon 511B may form a tubular shape annularly disposed about the central post 511A. In the expanded state 514, the balloon 511B may extend radially outward from the central post 511A. The gathering mechanism 510 is longitudinally displaceable relative to the retaining mechanism 250 between a retracted position 517 and an extended position 518 via proximal and distal displacement of a handle 515 as indicated by the arrow 516.

The central post 511A includes a drill bit 511C attached to the distal end of the central post 511A to facilitate forming a hole 41 (see FIG. 5E) extending through the fragment 40 via rotation of the drill bit 511C. The drill bit 511C is coupled with a rotating actuator 519 (e.g., a motor) disposed within the handle 515 so that the drill bit 511C rotates in accordance with activating the rotating actuator 519.

By way of summary, the operator may displace the gathering mechanism 510 between the retracted position 517 and the extended position 518. The operator may activate the rotating actuator 519 causing the drill bit 511C to rotate and drill a hole 41 through the fragment 40. The operator may insert the central post 511A through the hole 41 to position the balloon 511B distal the fragment 40. The operator may also transition the balloon 511B between the deflated state 513 and the expanded state 514 to retain the fragment 40 on the central post 411A.

Figures 5A, 5B, 5C:
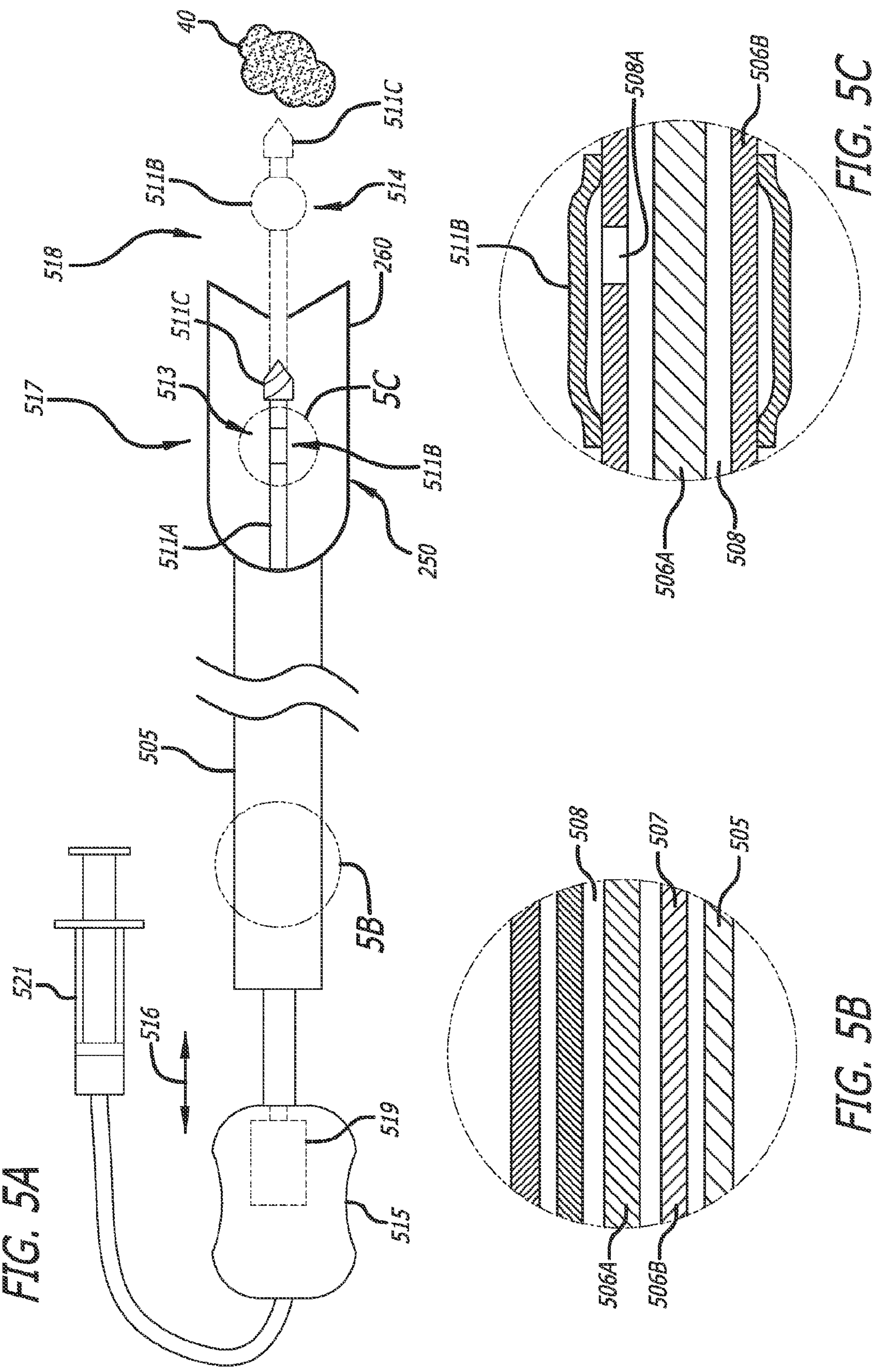
FIG. 5A illustrates a side view of a fourth embodiment of a retrieval instrument, in accordance with some embodiments.
FIG. 5B is a detailed cross-sectional view of the instrument shaft of FIG. 5A, in accordance with some embodiments.
FIG. 5C is a detailed cross-sectional view of the gathering mechanism of FIG. 5A, in accordance with some embodiments.

FIG. 5B is a detailed cross-sectional view of the shaft 505, in accordance with some embodiments. As shown, the shaft 505 includes a lumen 507 having elongate components 506 extending therethrough. The elongate components 506 include a central gathering shaft 506A and an annular gathering shaft 506B extending along the shaft 505, the central gathering shaft 506A and an annular gathering shaft 506B defining the central post 511A. The central gathering shaft 506A is disposed within a lumen 508 of the annular gathering shaft 506B. The central gathering shaft 506A and/or the annular gathering shaft 506B couples the gathering mechanism 510 with the handle 515 to define longitudinal co-movement of the gathering mechanism 510 and the handle 515. The rotating actuator 519 is coupled with the central gathering shaft 506A at the proximal end thereof so that the central gathering shaft 506A and drill bit 511C rotate together according to operation of the rotating actuator 519.

FIG. 5C is a detailed view of a distal portion of the gathering mechanism 510. In the exemplary illustrated embodiment, the balloon 511B is sealably coupled with the annular gathering shaft 506B and an orifice 508A defines fluid communication between the lumen 508 and the balloon 511B. By way of summary, the fluid device 521 (FIG. 5A) is fluidly coupled with the lumen 508 and the lumen is fluidly coupled with the balloon 511B so that manipulation of the fluid device 521 inflates and deflates the balloon 511B.

Figure 5D:
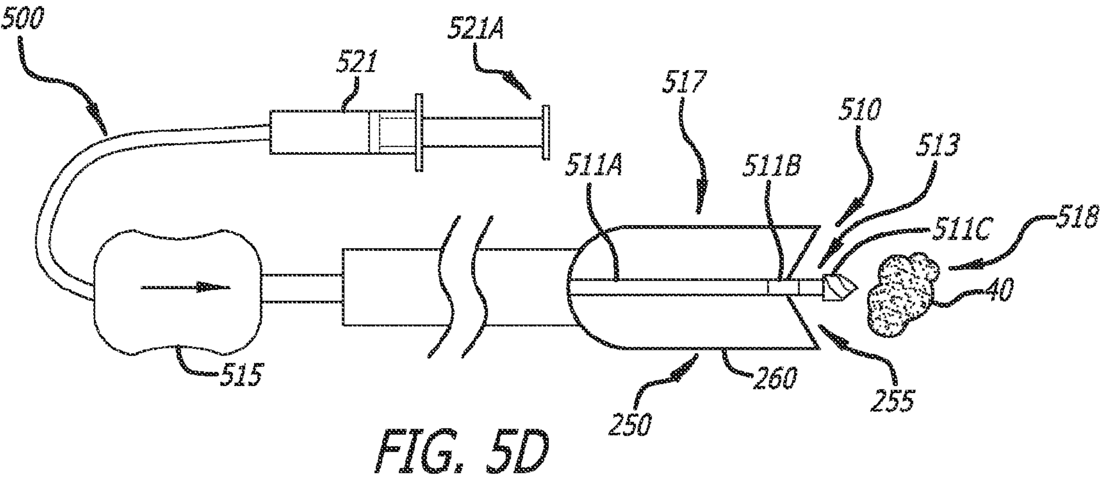
FIGS. 5D-5H illustrate the instrument of FIGS. 5A-5C in various states of a fragment retrieval process, in accordance with some embodiments.

FIGS. 5D-5H illustrate the instrument 500 in various states of a fragment retrieval process. In FIG. 5D, the gathering mechanism 510 is extended distally away from the retracted position 517 toward the extended position 518 with the balloon 511B remaining in the deflated state 513. As shown, the gathering mechanism 510 may be distally displaced to contact the fragment 40 with the drill bit 511C. The balloon 511B is in the deflated state 513 in accordance with the plunger 521A in the withdrawn position.

Figure 5E:
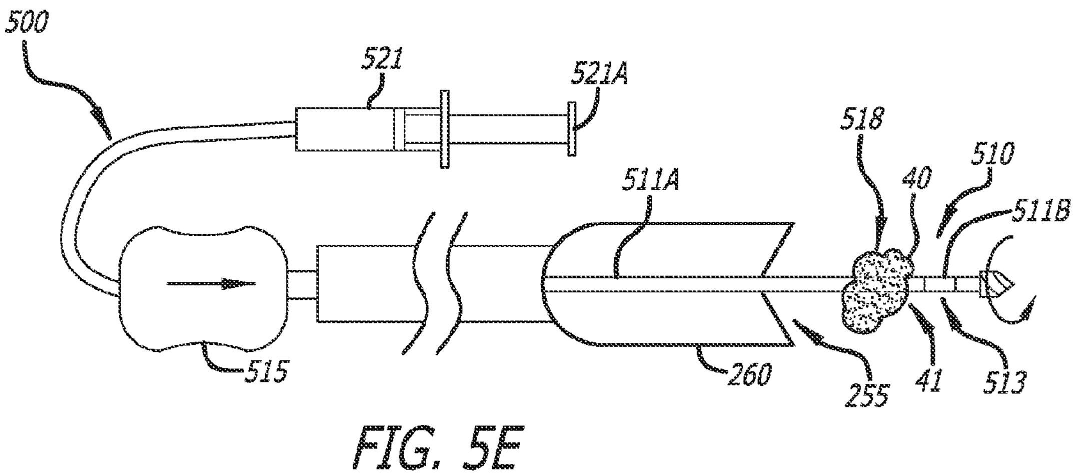

In FIG. 5E, the rotating actuator 519 is activated in combination with further distal displacement of the gathering mechanism 510 to form a hole 41 extending through the fragment 40. The gathering mechanism 510 is inserted through the hole 41 as the gathering mechanism 510 is further distally displaced to the extended position 518 thereby threading the fragment 40 onto the central post 511A. The handle 515 is also distally displaced in relation to the position of the handle 515 shown in FIG. 5A and the entryway 255 is in the closed configuration. The balloon 511B remains in the deflated state 513.

Figure 5F:
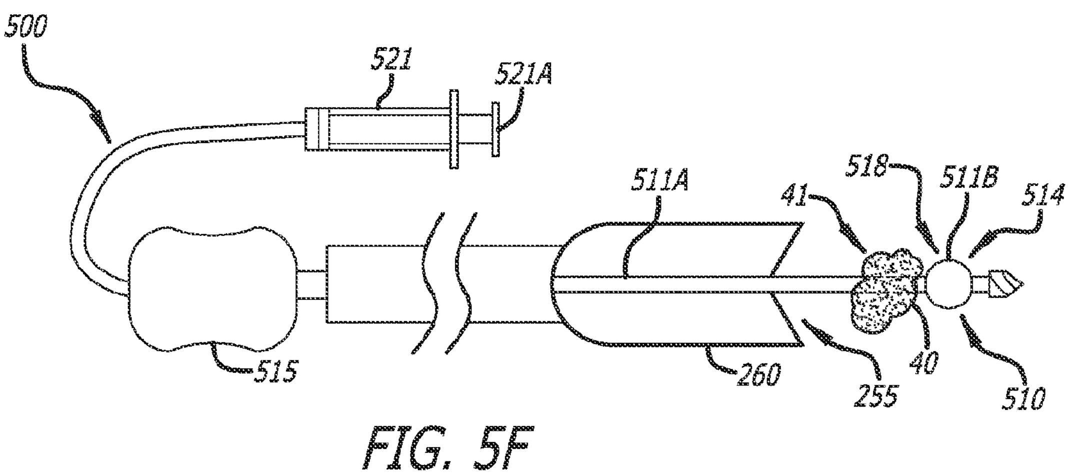

In FIG. 5F, the gathering mechanism 510 is in the extended position 518. The balloon 511B is transitioned to the inflated state 514 to extend radially outward beyond a circumference of the hole 41 in accordance with the plunger 521A displaced to the depressed position. The entryway 255 remains in the closed configuration.

Figure 5G:
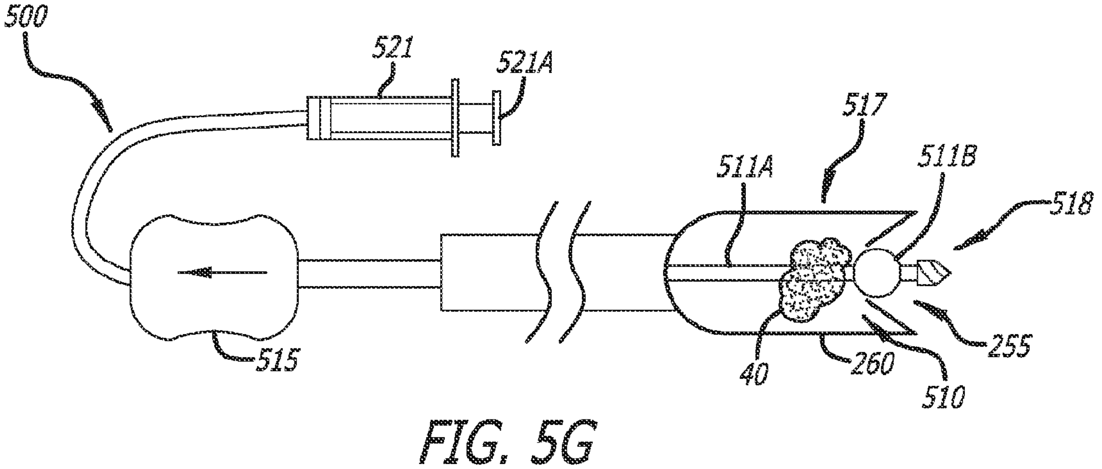

In FIG. 5G, the balloon 511B remains inflated state 514. The gathering mechanism 510 is retracted from the extended position 518 to the retracted position 517 so that the fragment 40 together with the gathering mechanism 510 is displaced through the entryway 255 into the container 260. During passage of the fragment 40 together with the gathering mechanism 510 through the entryway 255, the entryway 255 transitions from the closed configuration to the open configuration.

Figure 5H:
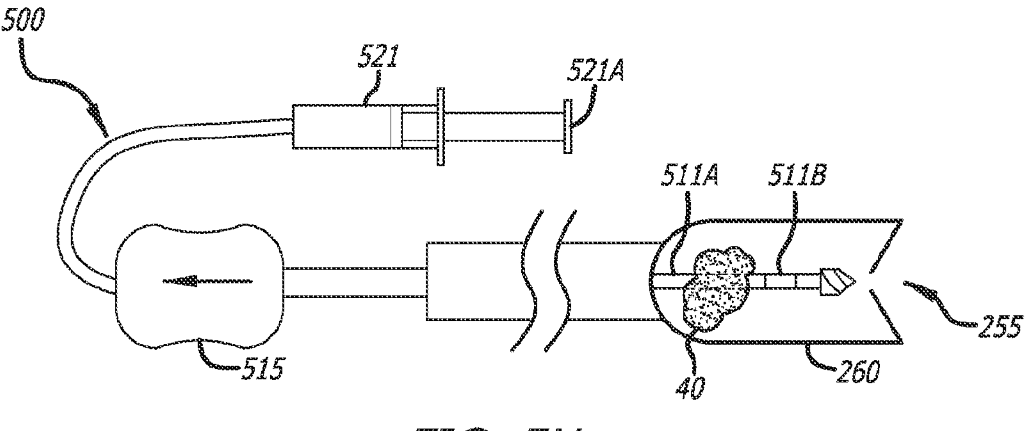

In FIG. 5H, the balloon 511B is transitioned to deflated state 513 as the plunger of syringe 521 displaced to the withdrawn position. The fragment 40 remains threaded onto the central post 511A. The entryway 255, as biased, returns to the closed configuration after the fragment 40 is fully within the container 260. The retrieval process of FIGS. 5C-5F may be repeated to gather and retain additional kidney stone fragments 40. In some embodiments, since the fragments 40 are retained on the central post 511A in accordance with the retrieval process, the retaining mechanism 250 may be omitted from the instrument 500.

In an alternative embodiment, the drill bit 511C and the rotating actuator 519 may be omitted. In such an embodiment, the fragment retrieval process may include extending the gathering mechanism 510 from the retracted position 517 to the extended position 518 to position the balloon 511B (in the deflated state) distally beyond the fragments 40. The balloon 511B is then inflated to trap the fragments 40 on the proximal side the balloon 511B. The gathering mechanism 510 is then retracted from the extended position 518 to the retracted position 517 to displace the fragments 40 through the entryway 255 into the container 260.

Figure 6A:
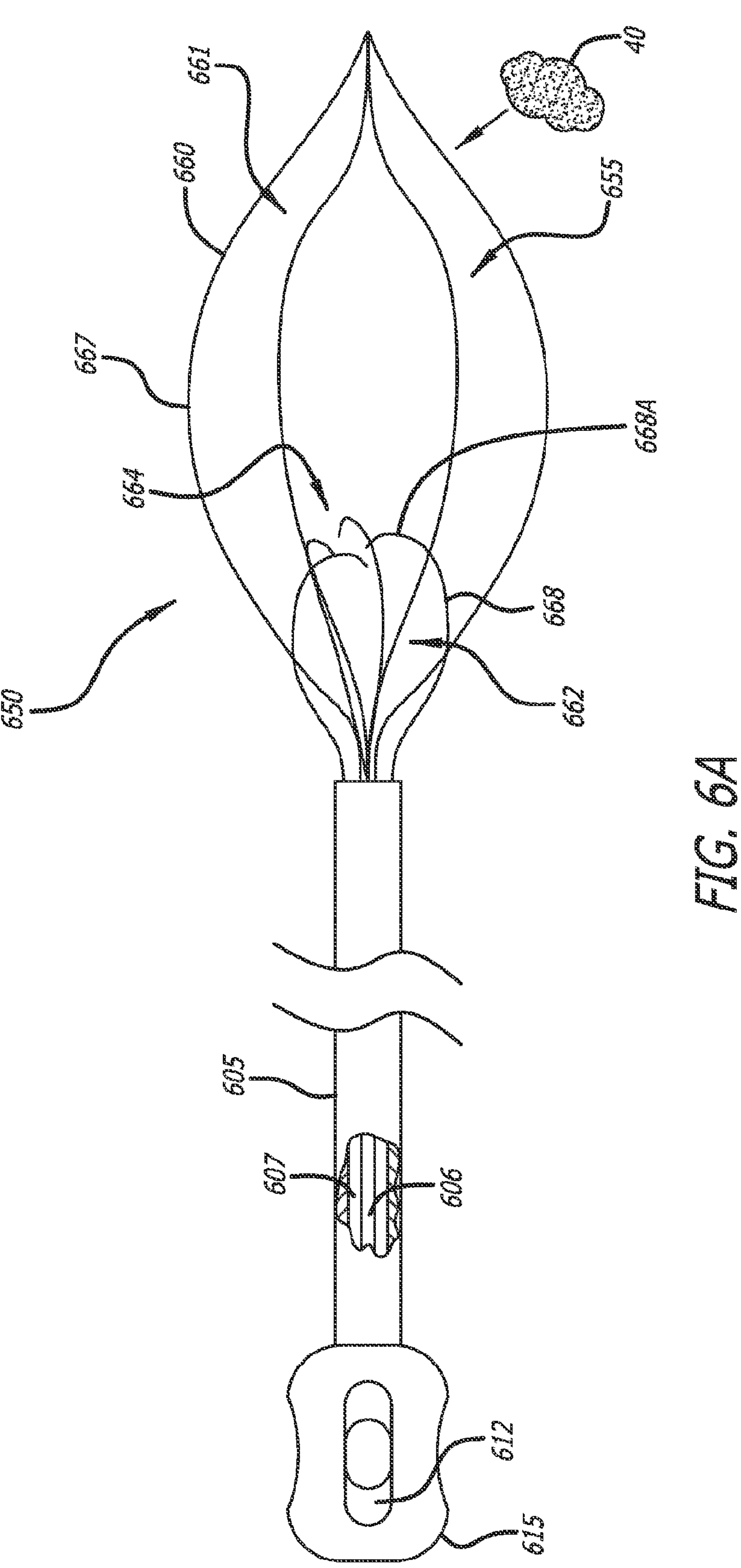
FIG. 6A illustrates a side view of a second embodiment of a retaining mechanism of FIG. 2A, in accordance with some embodiments.

FIG. 6A illustrates a second embodiment of a retaining mechanism 650. The retaining mechanism 650 may be employed as a stand-alone instrument or in combination with any of the gathering mechanisms disclosed herein for the retrieval and removal of kidney stone fragments from a patient. Although not shown in FIG. 6A and other figures that follow, reference to the ureteroscope 50 and components thereof as shown in FIGS. 1A-1B is made in the description below. The retaining mechanism 650 may be coupled with an elongate flexible shaft 605 (e.g., a guidewire) configured to extend along the working channel 54. The retaining mechanism 650 may be configured for insertion through the working channel 54. In some embodiments, the retaining mechanism 650 may transition between a collapsed state for disposition in the working channel 54 and an expanded state in accordance with operation outside of the working channel 54. Generally speaking, the retaining mechanism 650 may facilitate retention and removal of multiple stone fragments 40 from the patient.

In the illustrated embodiment, the retaining mechanism 650 may generally include a container 660 (e.g., a basket) with one or more entryways 655 for fragments 40 to enter the container 660. The container 660 may be sized to contain a plurality of stone fragments 40. The container 660 may include multiple wire elements 667 defining the structure of the container 660. The wire elements 667 may be formed of a metal, such as Nitinol, for example. In alternative embodiments, the wire elements 667 may be formed of a plastic material such as polyethylene, nylon, or any other suitable medical grade polymeric material.

The entryway 655 may be defined by spaces between the wire elements 667. The container 660 is configured to transition between an expanded receiving configuration and a contracted containing configuration. In the receiving configuration, passage of fragments 40 through the entryway(s) 655 is allowed, and in the containing configuration, passage of fragments 40 through the entryway(s) 655 is inhibited.

The container 660 includes a first compartment 661 and a second compartment 662. In some embodiments, the container 660 may include more than two compartments. In some embodiments, the second compartment 662 may be disposed proximal the first compartment 661. In some embodiments, the second compartment 662 may be disposed within the first compartment 661. The entryway(s) 655 provide for passage of fragments 40 into the first compartment 661. The container 660 includes a passageway 664 configured for passage of fragments 40 therethrough, i.e., from the first compartment 661 to the second compartment 662.

In an exemplary embodiment, the second compartment 662 may comprise a series of wire prongs 668. The prongs 668 may be spaced such that fragments exceeding a defined size limit are constrained within the second compartment 662. The prongs 668 may include a distal portions 668A extending radially inward through the spaces between the wire elements 667 of the first compartment 661. The distal portions 668A may define the passageway 664.

In some embodiments, the distal portions 668A may define a one-way passageway 664 allowing fragments 40 to enter the second compartment 662 and inhibiting fragments 40 from exiting the second compartment 662. By way of example, the distal portions 668A may extend in a proximal direction so as to deflect outward (i.e., in an open direction) upon engagement of fragments 40 passing from the first compartment 661 to the second compartment 662. Conversely, fragments 40 engaging the distal portions 668A from within the second compartment 662 may deflect the distal portions 668A radially inward (i.e., in a closed direction) preventing the fragments 40 from exiting the second compartment 662.

In some embodiments, the first compartment 661 and the second compartment 662 may define different enclosed volumes. For example, the second compartment 662 may define a larger volume than the first compartment 661 so that the second compartment 662 may contain a larger number or volume of fragments 40 (or more fragment matter) than the first compartment 661. In alternative embodiments, the first compartment 661 may define a larger volume than the second compartment 662.

The retaining mechanism 650 may include a handle 615 at a proximal end of the shaft 605 via which the operator may longitudinally displace and/or rotate the retaining mechanism 650. The retaining mechanism 650 may include one or more actuators 612 coupled with the handle 615. The actuators 612 may be coupled with the container 660, including the first compartment 661 and/or the second compartment 662, via one or more elongate members 606 extending along the shaft 605, and the actuators 612 may be configured to facilitate operations of the container 660 (e.g., transitioning the container 660 between the retrieving and containing configurations) via manipulation of the actuators 612 by the operator. The elongate members 606 may be disposed within a lumen 607 extending along the shaft 605.

In some embodiments, the operations may include proximally displacing the container 660 or a portion thereof within the lumen 607.

Figures 6B, 6C, 6D, 6E:
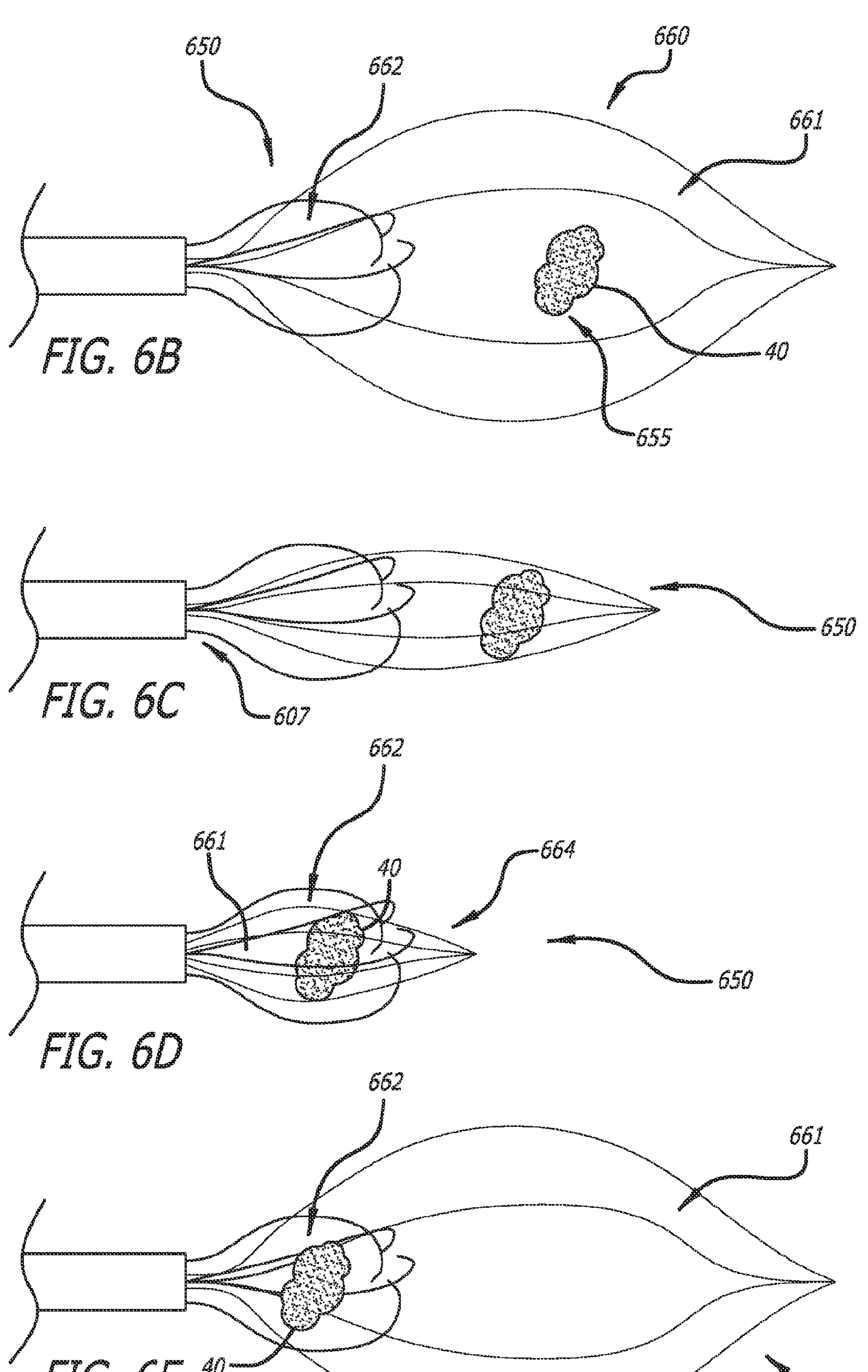
FIGS. 6B-6E illustrate the retaining mechanism of FIG. 6A in various states of a fragment retrieval process, in accordance with some embodiments.

FIGS. 6B-6E illustrate the retaining mechanism 650 in various states of a fragment retaining process. In FIG. 6B, the first compartment 661 is in the retrieving configuration. The fragment 40 is disposed within the first compartment 661 having entered therein through the entryway 655.

In FIG. 6C, the first compartment 661 is transitioned into the containing configuration so that the fragment 40 is constrained within the first compartment 661. The first compartment 661 is also proximally displaced so that a portion of the first compartment 661 is disposed within the lumen 607.

In FIG. 6D, first compartment 661 has also been further proximally displaced so that the fragment 40 is displaced though the passageway 664 into the second compartment 662.

In FIG. 6E, first compartment 661 has been transitioned back into the receiving configuration. The fragment 40 remains constrained within second compartment 662 via the one-way functionality of the passageway 664. The retaining process of FIGS. 5C-5F may be repeated to receive and retain additional kidney stone fragments 40.

Figure 7:
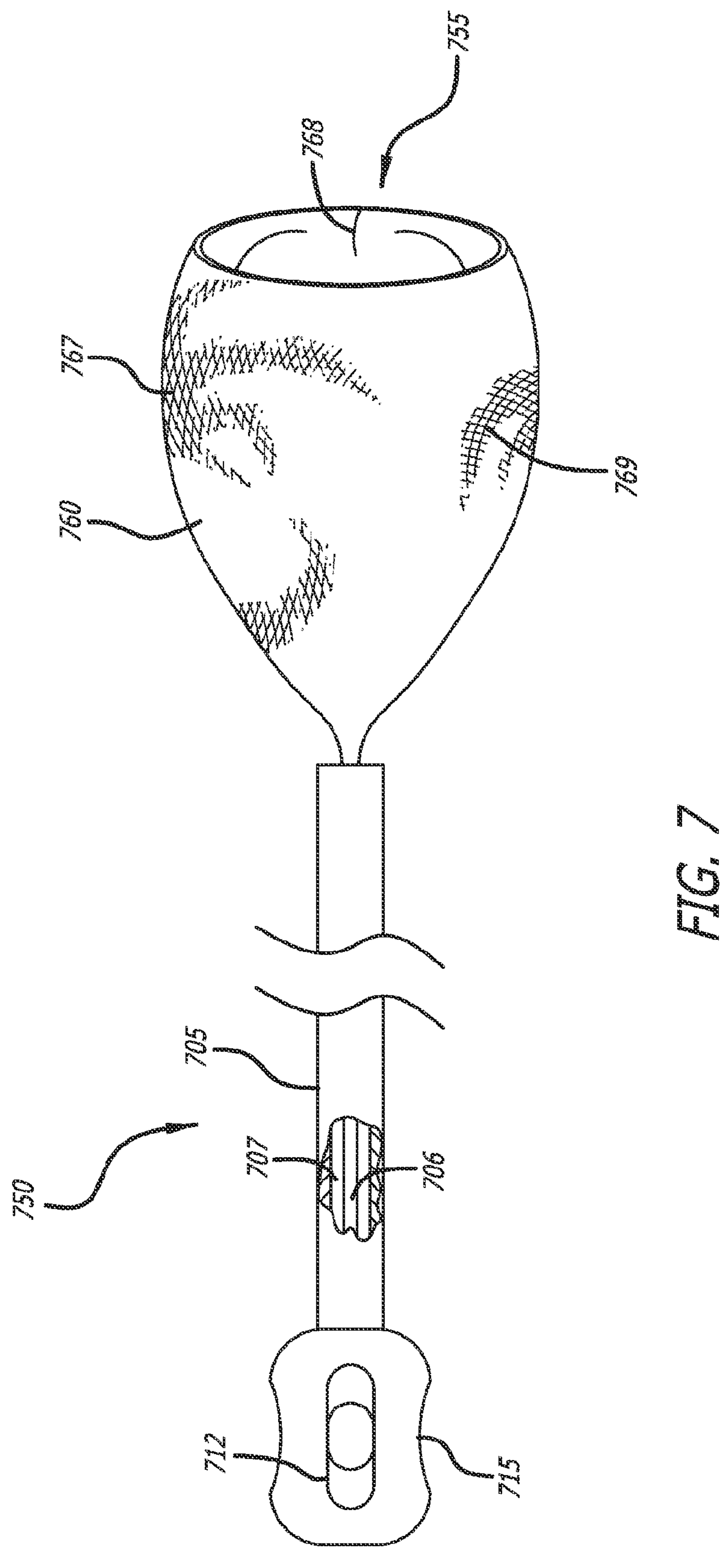
FIG. 7 illustrates a side view of a third embodiment of a retaining mechanism of FIG. 2A, in accordance with some embodiments.

FIG. 7 illustrates a third embodiment of a retaining mechanism 750. The retaining mechanism 750 may be employed as a stand-alone instrument or in combination with any of the gathering mechanisms disclosed herein for the retrieval and removal of kidney stone fragments from a patient. Although not shown in FIG. 7, reference to the ureteroscope 50 and components thereof as shown in FIGS. 1A-1B is made in the description below. The retaining mechanism 750 may be coupled with an elongate flexible shaft 705 (e.g., a guidewire) configured to extend along the working channel 54. The retaining mechanism 750 may be configured for insertion through the working channel 54. In some embodiments, the retaining mechanism 750 may transition between a collapsed state for disposition in the working channel 54 and an expanded state in accordance with operation outside of the working channel 54. Generally speaking, the retaining mechanism 750 may facilitate retention and removal of multiple stone fragments 40 from the patient.

In the illustrated embodiment, the retaining mechanism 750 may generally include a container 760 including an entryway 755 for fragments 40 to enter the container 760. The container 760 may be sized to contain a plurality of stone fragments 40. The container 760 may include multiple wire elements 767 defining the structure of the container 760. The wire elements 767 may be formed of a metal, such as Nitinol, for example. In some embodiments, the wire elements 767 may be formed of a plastic material such as polyethylene, nylon, or any other suitable medical grade polymeric material. The container 760 also include a thin flexible wall 769 which may also be formed of a suitable medical grade polymeric material. The wall 769 may prevent passage of fragments 40 through the spaces between the wire elements 767.

The entryway 755 may be positioned at a distal end of the container 760. The container 760 includes multiple prongs 768 extending radially inward at the entryway 755. The prongs 768 define a one-way functionality of the entryway 755 allowing fragments 40 to enter the container 760 and inhibiting fragments 40 from exiting the container 760. By way of example, the prongs 768 may extend in a proximal direction so as to deflect outward (i.e., in an open direction) upon engagement of fragments 40 passing through the entryway 755 into the container 760. Conversely, fragments 40 engaging the distal prongs 768 from within the container 760 may deflect the prongs 768 radially inward (i.e., in a closed direction) to prevent fragments 40 from exiting the container 760.

The retaining mechanism 750 may include a handle 715 at a proximal end of the shaft 705 via which the operator may longitudinally displace and/or rotate the retaining mechanism 750. The retaining mechanism 750 may include one or more actuators 712 coupled with the handle 715. The actuators 712 may be coupled with the container 760 via one or more elongate members 706 extending along the shaft 705, and the actuators 712 may be configured to facilitate operations of the container 760 (e.g., longitudinally displacing the container 760 with respect to the shaft 705) via manipulation of the actuators 712 by the operator. The elongate members 706 may be disposed with a lumen 707 extending along the shaft 705. In some embodiments, the operations may include proximally displacing the container 760 or a portion thereof within the lumen 707.

Figure 8:
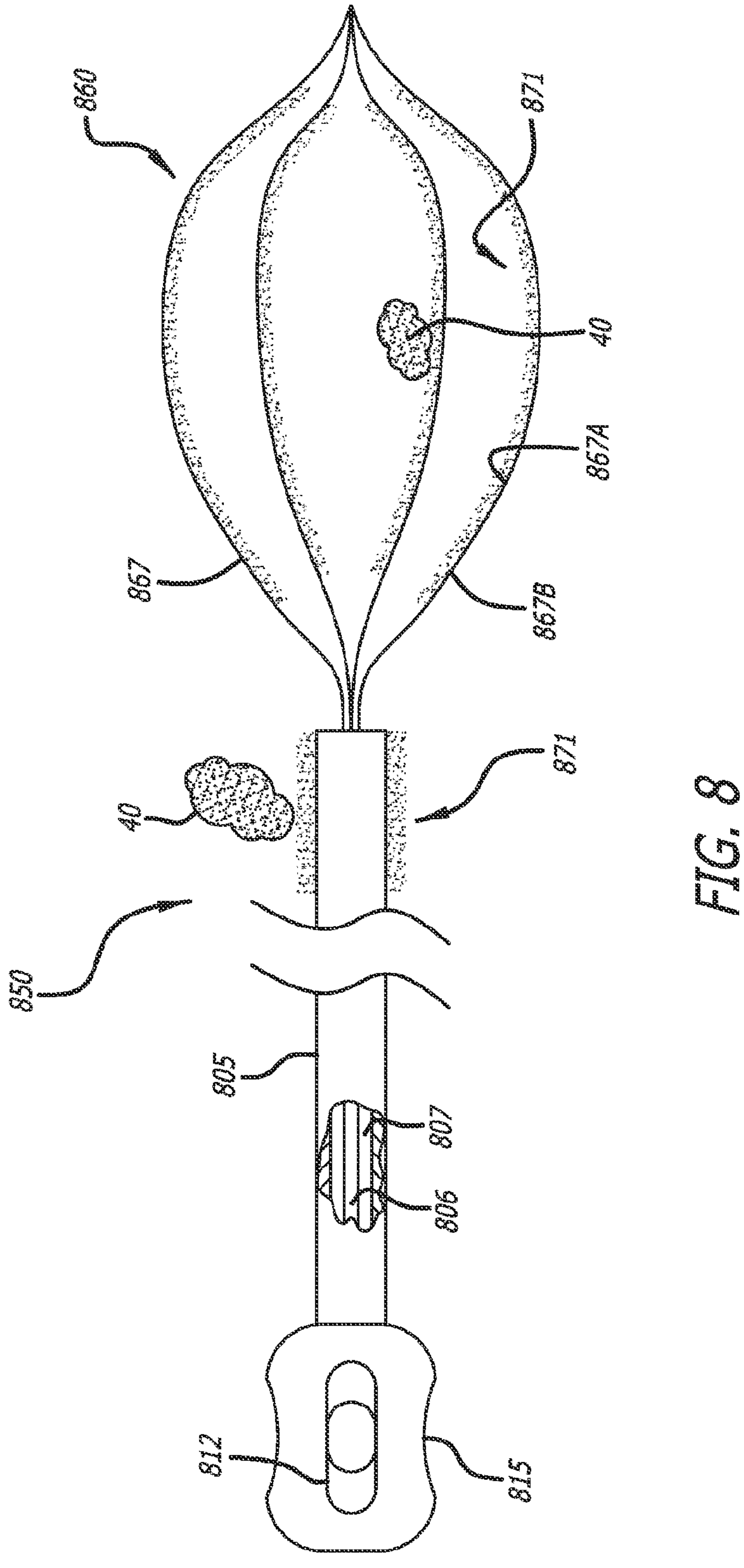
FIG. 8 illustrates a side view of a fourth embodiment of a retaining mechanism of FIG. 2A, in accordance with some embodiments.

FIG. 8 illustrates a fourth embodiment of a retaining mechanism 850. The retaining mechanism 850 may be employed as a stand-alone instrument or in combination with any of the gathering mechanisms disclosed herein for the retrieval and removal of kidney stone fragments from a patient. Although not shown in FIG. 8, reference to the ureteroscope 50 and components thereof as shown in FIGS. 1A-1B is made in the description below. The retaining mechanism 850 may be coupled with an elongate flexible shaft 805 (e.g., a guidewire) configured to extend along the working channel 54. The retaining mechanism 850 may be configured for insertion through the working channel 54. In some embodiments, the retaining mechanism 850 may transition between a collapsed state for disposition in the working channel 54 and an expanded state in accordance with operation outside of the working channel 54. Generally speaking, the retaining mechanism 850 may facilitate retention and removal of multiple stone fragments 40 from the patient.

In the illustrated embodiment, the retaining mechanism 850 may generally include a container 860 (e.g., a basket) including one or more entryway(s) 855 for fragments 40 to enter the container 860. The container 860 may be sized to contain a plurality of stone fragments 40. The container 860 may include multiple wire elements 867 defining the structure of the container 860. The wire elements 867 may be formed of a metal, such as Nitinol, for example. In some embodiments, the wire elements 867 may be formed of a plastic material such as polyethylene, nylon, or any other suitable medical grade polymeric material. The entryway(s) 855 may be defined by the spaces between the wire elements 867.

The container 860 may be configured to transition between an expanded receiving configuration and a contracted containing configuration. In the receiving configuration, passage of fragments 40 through the entryway(s) 855 is allowed, and in the containing configuration, passage of fragments 40 through the entryway(s) 855 is inhibited.

The retaining mechanism 850 may include a handle 815 at a proximal end of the shaft 805 via which the operator may longitudinally displace and/or rotate the retaining mechanism 850. The retaining mechanism 850 may include one or more actuators 812 coupled with the handle 815. The actuators 812 may be coupled with the container 860, including via one or more elongate members 806 extending along the shaft 805, and the actuators 812 may be configured to facilitate operations of the container 860 (e.g., longitudinally displacing the container 860 with respect to the shaft 805) via manipulation of the actuators 812 by the operator. The elongate members 806 may be disposed with a lumen 807 extending along the shaft 805. In some embodiments, the operations may include proximally displacing the container 860 or a portion thereof within the lumen 807 to define the containing configuration of the container 860.

The retaining mechanism 850 includes an adhesive coating 871 applied to the wire elements 867. The adhesive coating 871 is configured to attach the wire elements 867 to the fragments 40 upon contact therewith. In use, fragments 40 disposed within the container 860 contact the wire elements 867 and become attached to the wire elements 860. In some embodiments, the adhesive coating 871 may be applied to an inside surface 867A of the wire elements 867 (i.e., the surface facing the interior of the container 860). In other embodiments, the adhesive coating 871 may also be applied to an outside surface 867B of the wire elements 867 (i.e., the surface facing the exterior of the container 860) so that fragments 40 may be attached to the exterior of the container 860. In some embodiments, the adhesive coating 871 may include a hydrogel which may in some embodiments define a lubrication between the wire elements 867 and an inside surface of the working channel 54 when the retaining mechanism 850 is advanced and/or retracted therethrough. In some embodiments, the hydrogel may be configured to swell during use.

In some embodiments, the adhesive coating 871 may also be applied to the shaft 805 (e.g., along a portion of a length of the shaft 805). In such embodiments, fragments 40 may also be attached to the shaft 805.

In use, the fragments 40 may be gathered into the container 860 through the entryways 855. Once fragments 40 are disposed within the container 860, the container 860 may be transitioned from the receiving configuration to the containing configuration thereby facilitating contact of the gathered fragments 40 with the wire elements 867 so that the adhesive coating 871 may attach the fragments 40 to the wire elements 867. The container 860 may then be transitioned back to the receiving configuration to receive additional fragments 40.

FIGS. 9A and 9B illustrate a fifth embodiment of retaining mechanism 950. The retaining mechanism 950 may be employed as a stand-alone instrument or in combination with any of the gathering mechanisms disclosed herein for the retrieval and removal of kidney stone fragments from a patient. FIG. 9A is a perspective illustration of a portion of the retaining mechanism 950, and FIG. 9B is a side view illustration of the retaining mechanism 950. The retaining mechanism 950 includes a flexible elongate instrument shaft 905 configured to extend along the working channel 54. The retaining mechanism 950 may be configured for insertion through the working channel 54. In some embodiments, the retaining mechanism 950 may transition between a collapsed state for disposition in the working channel 54 and an expanded state in accordance with operation outside of the working channel 54. Generally speaking, the retaining mechanism 950 may facilitate retention and removal of multiple stone fragments 40. In some embodiments, the retaining mechanism 950 may include functionalities associated with gathering fragments 40 into the retaining mechanism 950.

In some embodiments, the retaining mechanism 950 may be configured for separation from the ureteroscope 50 via the proximal end of the shaft 905A. In other words, components coupled to the shaft 905 at the proximal end 905A may be configured for separation from the shaft 905 so that the working channel 54 may be threaded off the shaft 905 via the proximal end 905A.

In the illustrated embodiment, the retaining mechanism 950 may generally include a container 960 having an entryway 955 (i.e., an opening) for fragments 40 to enter the container 960. The container 960 may be sized to contain a plurality of stone fragments 40. The container 960 may include a flexible or semi-flexible wall 965 which may, in some embodiments, define a tubular shape. The container 960 may be formed of a plastic material such as polyethylene, polyvinylchloride, silicone, or any other suitable medical grade polymeric material.

The entryway 955 may transition between an open configuration and a closed configuration. In the open configuration, passage of fragments 40 through the entryway 955 is allowed, and in the closed configuration, passage of fragments 40 through the entryway 955 is inhibited. In the illustrated embodiment, the entryway 955 may be biased toward the closed configuration.

The container 960 includes a flexible elongate member 906 extending along the shaft 905. A distal portion 906A of the elongate member 906 extends along a circumference of the container 960 at the entryway 955. The elongate member 906 is coupled with the container wall 965 along the circumference at the entryway 955. The coupling of the elongate member 906 with the container wall 965 is configured so that the elongate member 906 may perform a drawstring functionality. In other words, the elongate member 906 is coupled with the container wall 965 so that proximal displacement of the elongate member 906 along the shaft 905 cinches or otherwise closes off the entryway 955. By way of summary, proximal and distal displacement of the elongate member 906 along the shaft 905 transitions the entryway 955 between the closed configuration and the closed configuration, respectively. The elongate member 965 may be formed of a guidewire, a cable, or any suitable structure for providing a tensile force. The material of the elongate member 965 may be a metal or a plastic.

With further reference to FIG. 9B, in some embodiments, the shaft 905 may include a lumen 907 extending along a length of the shaft 905 between the container 960 and the proximal end 905A. In further embodiments, the shaft 905 may be coupled with a fluid device 921 (e.g., a syringe) having a plunger 921A. In use, the plunger 921A may be displaced between a depressed position “D” and a withdrawn position “W” causing proximal and distal fluid flow 904 within the lumen 907. More specifically, depressing the plunger 21A causes fluid flow 904 to enter the container 960 via the lumen 907, and withdrawing the plunger 921A causes fluid flow 904 to exit the container 960 via the lumen 907.

Figures 9D, 9E, 9F:
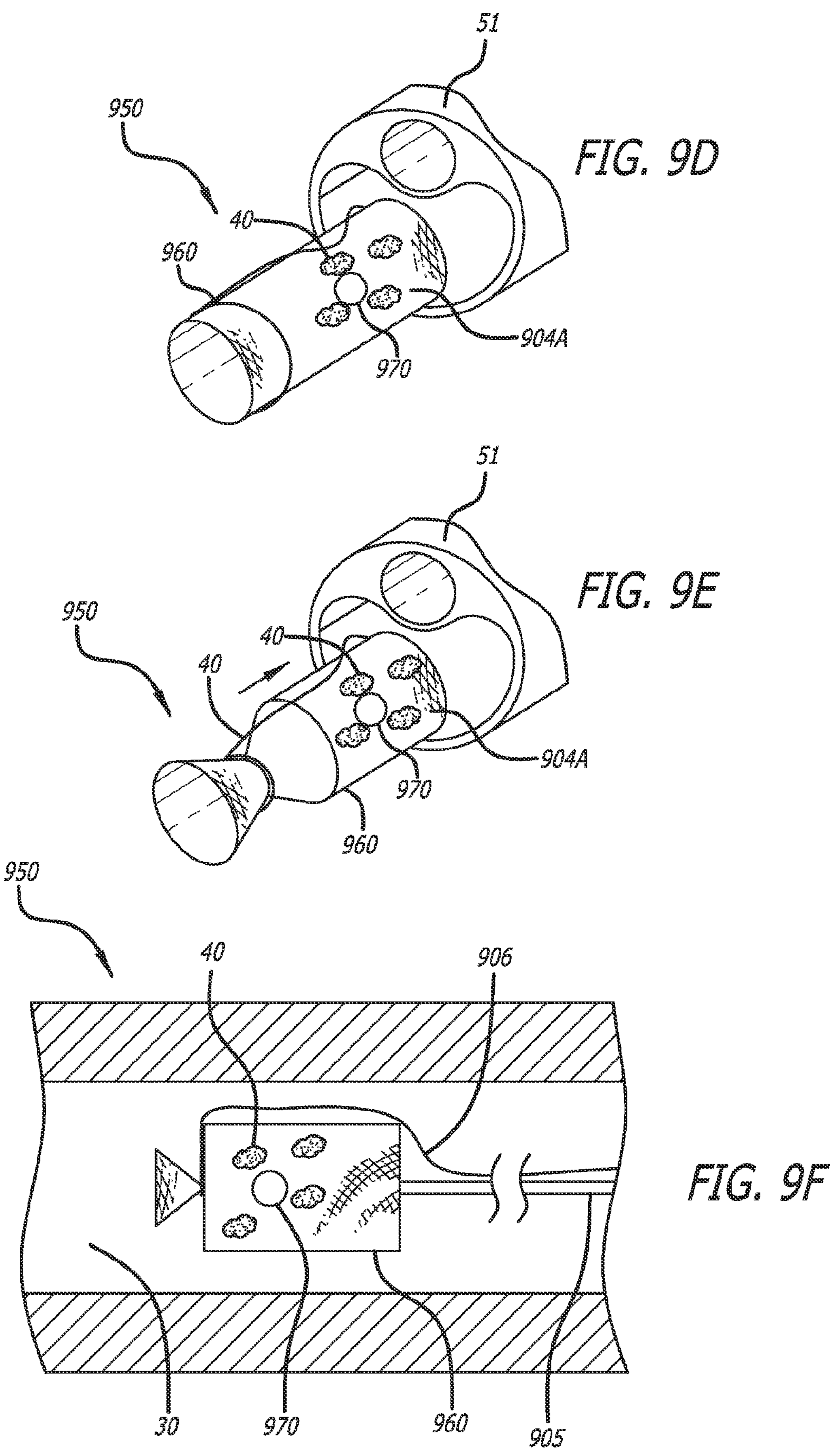

FIGS. 9C-9H illustrate the retaining mechanism 950 in various states of a fragment retaining process. In FIG. 9C, the container 960 is extended beyond a distal end 57 of the ureteroscope shaft 51. As shown, the entryway 955 is disposed in the open configuration to receive fragments 40 therethrough. In some embodiments, a fragment 40 may be urged through the entryway 955 via a fluid force 909 exerted on the fragment 41, the fluid force 909 may be defined by a proximal fluid flow 904 as the plunger 921A (FIG. 9B) is withdrawn.

In FIG. 9D, multiple fragments 40 are disposed in the container 960. A chemical substance 970 is disposed within the container 960 to alter the chemical condition of the fluid 904A within the container. The substance 970 may include components (e.g., vinegar) configured to dissolve or reduce the size of the fragments 40. The substance 970 may be in a solid, liquid, or gel phase at various points during the retrieval process. In some embodiments, the substance 970 may transition from an inactive state to an active state.

In some embodiments, the substance 970 may be coupled with the container 960. For example, a portion of an inside surface of the container 960 may be coated with the substance 970. In some embodiments, the substance 970 be located adjacent the entryway 955 so that the substance 970 may be activated as a result of closing off the entryway 955.

In some embodiments, the substance 970 may be dispensed within the container 960 after the retrieval process is initiated. In further embodiments, the substance 970 may be dispensed within the container 960 after the entryway 955 is closed off. In an exemplary embodiment, the substance 970 may be transferred from the fluid device 921 to the container 960 via distal fluid flow 904 through the lumen 907.

In FIG. 9E, the entryway 955 is closed off via proximal displacement of the elongate member 906. In some embodiments, closing off the entryway 955 may physically and/or chemically isolate the contents of the container 960 (e.g., the substance 970) from the patient. In the closed off state, the substance 970 may alter the chemical condition of the fluid 904A to facilitate the reduction of fragment size over a defined time period.

In some embodiments, with the container 960 in closed off state, the chemical condition of the fluid 904A within the container may be further altered. For example, a portion of the fluid 904A may be withdrawn from the container 960 via the fluid device 921 and replaced with another fluid (not shown). The replacement fluid may include additional substance 970 or some other substance configured to further reduce the size of the fragments 40.

In some embodiments, the fluid device 921 may be used to draw a vacuum within the container 960. The vacuum may facilitate enhanced contact of the substance 970 with the fragments 40. In some embodiments, the substance 970 may cause the container 960 to dissolve.

In FIG. 9F, the ureteroscope shaft 51 is removed from the urinary tract 30 of the patient and the container 960 remains within the urinary tract 30. The shaft 905 extends along the urinary tract 30 so that the proximal end 905A (FIG. 9B) is disposed outside of the patient.

In some embodiments, the status of the fragments 40 (e.g., the size or number of fragments 40) may be observed via ultrasound or X-ray imaging systems (not shown). For example, the size of one or more fragments 40 within the container 960 may be too large for removal along urinary tract 30 at a first point in time as determined via observation. At a subsequent point in time, the fragments 40 may be small enough for removal along urinary tract 30 as determined via subsequent observation.

Figure 9G:
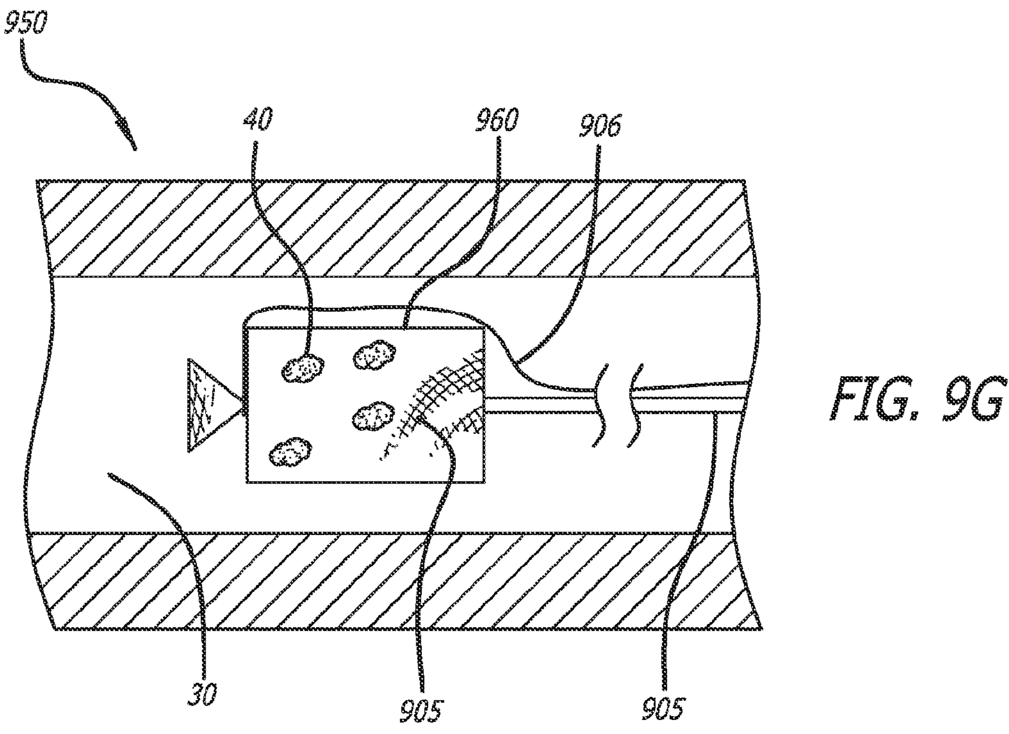

In FIG. 9G, the substance 970 of FIGS. 9D-9F has altered the chemical composition of the liquid 904A to define a liquid 904B that is chemically configured to cause decomposition of the stones/fragments 40. The retaining mechanism 950 may remain inserted into the urinary tract 30 for a time period during which the stones/fragments 40 decompose. The time period may be predefined or continue until the visual observation has determined that the fragments 40 are small enough for removal through the urinary tract 30.

In some embodiments, the features and functionalities of the retaining mechanism 950 may be combined with features and functionalities of the retaining mechanism 650 described above in relation to FIGS. 6A-6E, specifically the inclusion of multiple compartments. In such embodiments, the fragments 40 may be received into the first compartment and then transferred to the second compartment. The substance 970 may be dispensed into the second compartment to define the liquid 904B within the second compartment. The vacuum may be drawn within the second compartment to shrink the containment volume of the second compartment. A reduced containment volume may facilitate contact of the liquid 940B with the fragments 40 and/or define a desired concentration of the substance 970 within the liquid 940B.

Figure 9H:
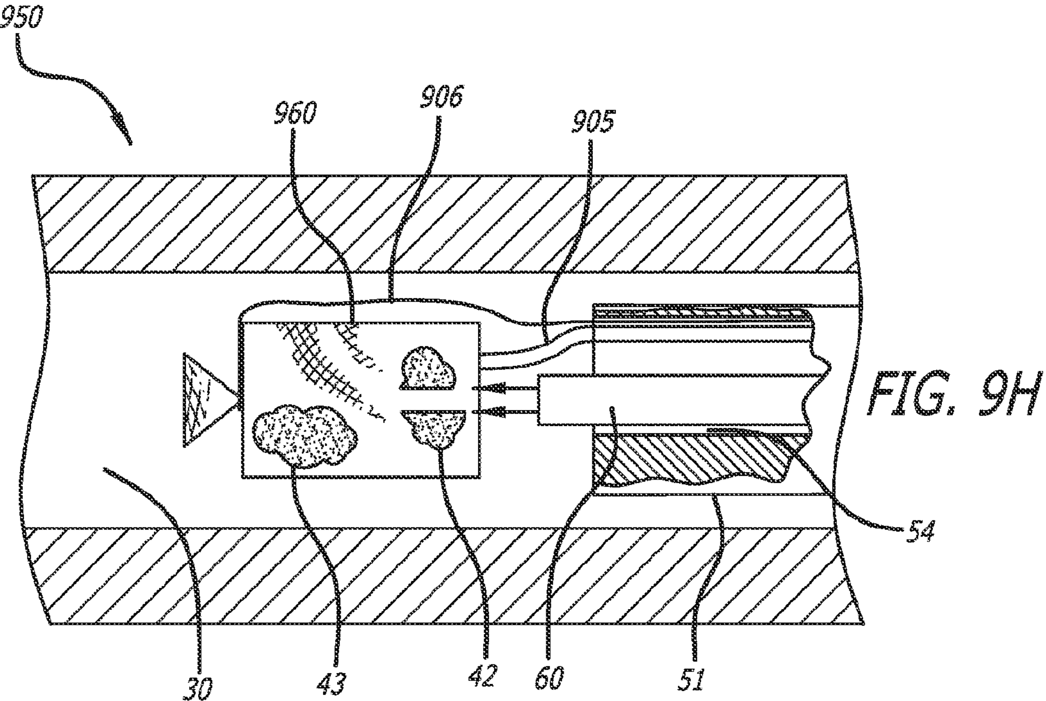

FIG. 9H illustrates a use case of the retaining mechanism 950. In this case a multiple stones/fragments 42 and 43 are enclosed in the container 960. The ureteroscope shaft 51 is inserted within the urinary tract 30 and a fiber optic laser 60 is inserted within the working channel 54. In the illustrated embodiment, the laser 60 is inserted within the working channel 54 together with the shaft 905 and the elongate member 906. In other embodiments, the shaft 905 and the elongate member 906 may be disposed in the urinary tract 30 alongside the ureteroscope shaft 51.

In this use case, the laser 60 is aimed at the stone 42 and activated to fragment the stone 42. The stone 43 is positioned away from the laser 60 and is therefore unaffected by the laser 60. At a subsequent time, the stone 43 is fragmented by the laser 60.

Figure 9I:
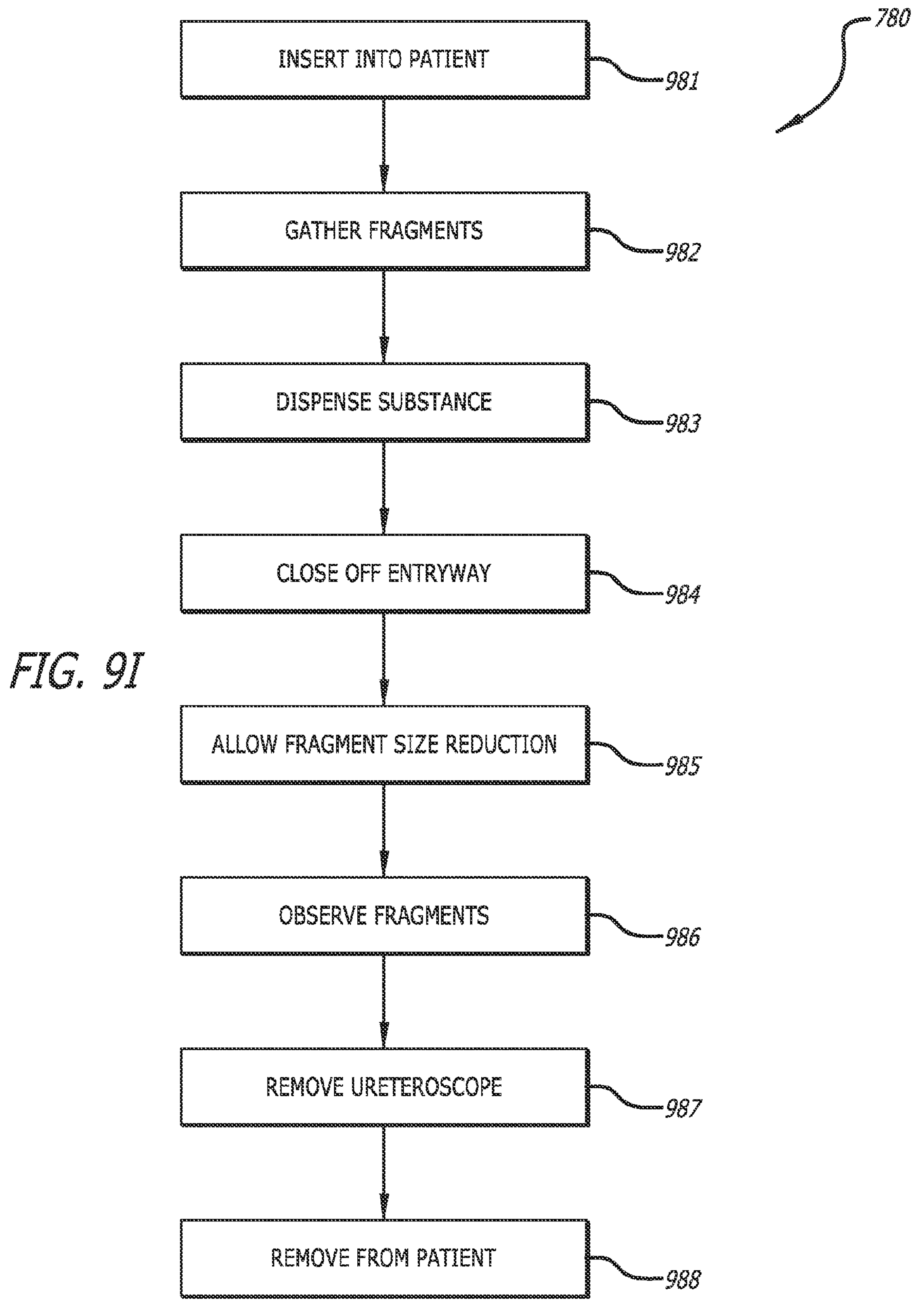
FIG. 9I is a flow chart of an exemplary fragment retrieval process, in accordance with some embodiments.

FIG. 9I illustrates flow chart of an exemplary process 980 for removing fragments 40 from the patient using the retaining mechanism 950. The retaining mechanism 950 is inserted into the patient (step 981) including inserting the retaining mechanism 950 through the working channel 54 of the ureteroscope shaft 51. Step 981 may further include collapsing the retaining mechanism 950 to facilitate disposition of the retaining mechanism 950 within the working channel 54. Step 981 may further include extending the retaining mechanism 950 beyond the distal end 57 of the ureteroscope shaft 51 and may also further include expanding the retaining mechanism 950 away from the collapsed state.

The process 980 further includes gathering fragments 40 into container 960 (step 982). The step 982 may include proximal and/or distal displacement of retaining mechanism 950 within the working channel 54 to position the entryway 955 adjacent a fragment 40. In some embodiments, step 982 may include defining a flow of fluid through the entryway 955 into the container 960 to drag the fragments 40 into the container 960.

The process 980 further includes dispensing the substance 970 into the container 960 so that the substance 970 is disposed in fluid contact with the fragments 40 (step 983). In some embodiments, the substance 970 may be attached to the container 960 so that dispensing the substance 970 is performed along with steps 981, 982. In some embodiments, step 983 may include activating the substance via a mechanical action such as closing off the entryway 955. In other embodiments, step 983 may include dispensing the substance 970 through the lumen 907 of the retaining mechanism 950.

The process 980 further includes closing off the entryway 955 (step 984) to prevent fragments 40 and/or the substance 970 from exiting the container 960. Step 984 may include proximally displacing the elongate member 906 to cinch down a circumferential portion of the container 960 adjacent the entryway 955.

The process 980 further includes allowing the substance 970 to breakdown or otherwise reduce the size of the contained fragments 40 (step 985).

The process 980 may include visually observing the contained fragments 40 to assess the size reduction progress (step 986). Observation may include utilizing ultrasound or X-ray equipment. Step 986 may specifically include visually assessing the size of fragments 40 in relation to predetermined size limit consistent with removal of fragments 40 via the urinary tract 30.

The process 980 may include removing the ureteroscope 50 from the urinary tract 30 of the patient while leaving the retaining mechanism 950 inserted within the urinary tract 30 (step 987).

The process 980 further includes removing retaining mechanism 950 from the urinary tract 30 (step 987). In some embodiments, the step 988 may be performed after visual observation has determined that the sizes of fragments 40 are below the size limit for removal through the urinary tract 30.

In some embodiments of the process 980, the retaining mechanism 950 may be removed from the urinary tract 30 by extracting the retaining mechanism 950 (step 987) from the working channel 54 of the ureteroscope 50 while the ureteroscope 50 remains within the urinary tract 30. In such embodiments, the retaining mechanism 950 may be extracted after visual observation has determined that the sizes of fragments 40 below the size limit for removal through the working channel 54.

Figure 9J:
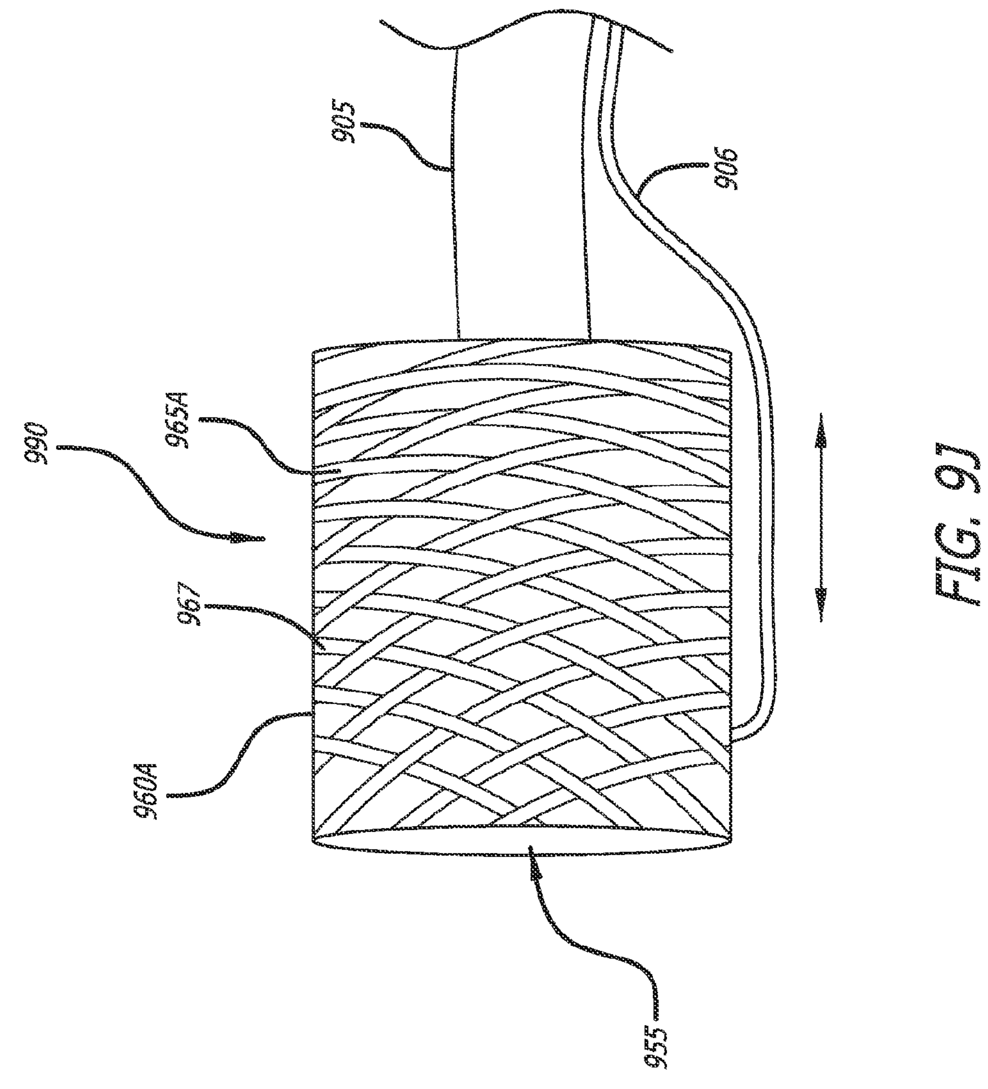
FIG. 9J is illustrates a second embodiment of a container of FIG. 9A, in accordance with some embodiments.

FIG. 9J illustrates a second embodiment of a container 960A for employment with the retaining mechanism 950. The container 960A defines a wall 965A including elongate elements 967 arranged to define a woven structure 990. The woven structure 990 is configured to decrease a diameter of the container 960A when a length of the container 960A is increased and vice versa in a manner similar to a Chinese finger trap.

The flexible elongate member 906 is coupled with the elongate elements 967 to facilitate increasing the length of the container 960A when the elongate member 906 is distally displaced along the shaft 905. In other words, the elongate member 906 is coupled with the container wall 965A so that distal displacement of the elongate member 906 along the shaft 905 closes off the entryway 955. By way of summary, proximal and distal displacement of the elongate member 906 along the shaft 905 transitions the entryway 955 between the open configuration and the closed configuration, respectively. Alternatively, the woven structure 990 decrease a diameter of the container 960A via rotation of a proximal portion of the container 960A with respect to a distal portion of the container 960A In an alternative embodiment, the woven structure 990 may be configured to decrease a diameter of the container 960A via rotation of a first portion of the container 960A with respect to a second portion of the container 960A defining a twisting or winding up condition of the container 960. In such an embodiment, the winding up condition may effectively close off the entryway 955.

Figure 10:
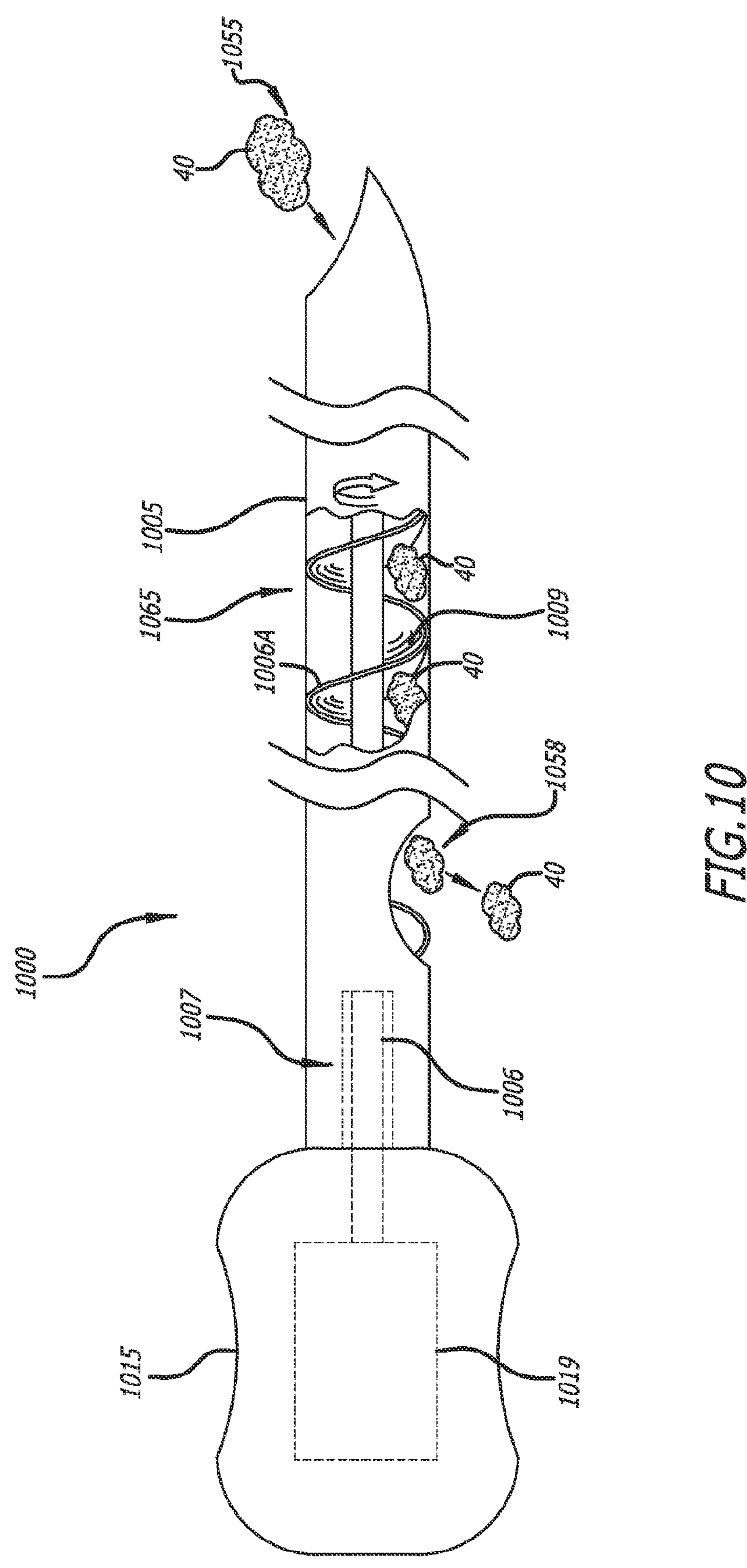
FIG. 10 illustrates a side view of a sixth embodiment of a retaining mechanism of FIG. 2A, in accordance with some embodiments.

FIG. 10 illustrates a sixth embodiment of retaining mechanism 1000. The retaining mechanism 1050 may be employed as a stand-alone instrument or in combination with any of the gathering mechanisms disclosed herein for the retrieval and removal of kidney stone fragments from a patient. Although not shown in FIG. 10, reference to the ureteroscope 50 and components thereof as shown in FIGS. 1A-1B is made in the description below. The retaining mechanism 1000 is configured for insertion through the working channel 54. Generally speaking, the retaining mechanism 1000 may facilitate retention and removal of multiple stone fragments 40.

In the illustrated embodiment, the retaining mechanism 1000 includes a shaft 1005 having a lumen 1007 extending therethrough between a distal entryway 1055 through which fragments 40 enter the lumen 1007 and a proximal exit 1058 through which the fragments 40 exit the lumen 1007. The shaft 1005 may be sized to contain a plurality of stone fragments 40 within the lumen 1007. The shaft 1005 includes an annular wall 1065. The wall 1065 may be formed of a plastic material such as polyethylene, polyvinylchloride, polypropylene, or any other suitable medical grade polymeric material.

The shaft 1005 includes a flexible rotating member 1006 extending along the shaft 1005. The rotating member 1006 includes an auger blade 1006A extending along the shaft 1005 between the entryway 1055 and the exit 1058. The rotating member 1006 may be formed of a metal or a plastic.

The retaining mechanism 1000 includes a rotating actuator 1019 disposed within a housing 1015 coupled with the shaft 1005. The rotating actuator 1019 is coupled with the rotating member 1006 so that the rotating member 1006 rotates in accordance with operation of the rotating actuator 1019. The auger blade 1006A is configured to proximally displace fragments 40 disposed within the lumen 1007 from the entryway 1055 to the exit 1058 during rotation of the auger blade 1006A. In use, the shaft 1005 is inserted through the working channel so that the entryway 1055 extends beyond the distal end 57 (see FIG. 1A) of the working channel 54 and so that the exit 1058 is located proximal the access port 55.

In use, fragments 40 are urged through the entryway 1055 into the lumen 1007. The rotating auger blade 1006A proximally displaces the fragments 40 along the shaft 1005. In some instances, the fragments 40 are proximally displaced along the shaft 1005 to the exit 1058 so that the fragments 40 are removed from the patient along the way. The fragments 40 may then exit the lumen 1007 via the exit 1058. In other instances, rotation of the auger blade 1006A may be discontinued while fragments 40 are disposed within the lumen 1007. In this instance, the fragments 40 are removed from the patient coincident with removal of the retaining mechanism 1000 from the patient. In some embodiments, the rotating auger blade 1006A may optionally include small ridges, notches, bumps or compartments (collectively, illustrated by ridges 1009) on the auger blade to assist in retaining the fragments 40.

Embodiments of the invention may be embodied in other specific forms without departing from the spirit of the present disclosure. The described embodiments are to be considered in all respects only as illustrative, not restrictive. The scope of the embodiments is, therefore, indicated by the appended claims rather than by the foregoing description. All changes that come within the meaning and range of equivalency of the claims are to be embraced within their scope.

What is claimed is:

1. A medical instrument for removing a kidney stone from a urinary tract of a patient body, comprising:

a flexible elongate shaft defining a proximal end and a distal end, the flexible elongate shaft configured for insertion within the urinary tract; and a retaining mechanism coupled with the flexible elongate shaft at the distal end, the retaining mechanism configured to retain a plurality of stone fragments within a container thereof, wherein:

the container comprises an entryway for the plurality of stone fragments to enter the container, the entryway is transitionable between:

an open state allowing passage of fragments therethrough, and a closed state inhibiting passage of fragments therethrough, and the entryway is configured to transition from the closed state to the open state by one or more of the plurality of stone fragments as the one or more of the plurality of stone fragments are moved into the retaining mechanism.

2. The instrument of claim 1, wherein the instrument is configured for insertion through a working channel of a ureteroscope.

3. The instrument of claim 2, wherein the retaining mechanism is collapsible to accommodate advancement through the working channel.

4. The instrument of claim 2, wherein, in use, a portion of the retaining mechanism is disposed within the working channel of the ureteroscope.

5. The instrument of claim 2, wherein, in use, one or more fragments are disposed within the working channel of the ureteroscope.

6. The instrument of claim 2, wherein the retaining mechanism is coupled with a distal tip of the ureteroscope so that upon articulation of the distal tip, the retaining mechanism articulates therewith.

7. The instrument of claim 1, wherein the retaining mechanism is configured to couple with the fragments so that proximal displacement of the retaining mechanism causes proximal displacement of the fragments.

8. The instrument of claim 1, wherein the retaining mechanism is configured to sequentially receive two or more fragments.

9. The instrument of claim 1, wherein the retaining mechanism is configured for attachment to the fragments.

10. The instrument of claim 9, wherein the retaining mechanism comprises an adhesive applied to the retaining mechanism.

11. The instrument of claim 10, wherein the adhesive comprises a hydrogel.

12. The instrument of claim 10, wherein:

the flexible elongate shaft is coated with the adhesive, and in use, the fragments are attached to the flexible elongate shaft via the adhesive.

13. The instrument of claim 1, wherein the container is configured to enclose the plurality of stone fragments.

14. The instrument of claim 13, wherein the container comprises a tubular shape.

15. The instrument of claim 13, wherein:

the container comprises a first compartment and a second compartment, in use, the fragments enter the first compartment, and the fragments are subsequently displaced from the first compartment into the second compartment.

16. The instrument of claim 13, wherein the container comprises a chemical substance configured to dissolve the fragments.

17. The instrument of claim 13, wherein the container comprises a flexible container wall.

18. The instrument of claim 17, wherein the flexible container wall is impervious to fluid.

19. The instrument of claim 13, wherein the container is a basket composed of wire elements.

20. The instrument of claim 19, wherein a diameter of the wire elements is between one to three French, inclusive.

21. The instrument of claim 19, wherein the wire elements are coated with an adhesive.

22. The instrument of claim 13, wherein the flexible elongate shaft comprises a lumen extending between the proximal end and the distal end.

23. The instrument of claim 22, wherein, in use, a portion of the retaining mechanism is disposed within the lumen.

24. The instrument of claim 22, wherein the lumen is in fluid communication with the container.

25. The instrument of claim 22, wherein the entryway is configured for disposition between the open state and the closed state in accordance with proximal fluid flow and distal fluid flow through the lumen, respectively.

26. The instrument of claim 22, wherein the container is configured so that proximal fluid flow through the lumen draws fragments toward the entryway.

27. The instrument of claim 22, wherein the container is configured so that proximal fluid flow through the lumen draws fragments through the entryway into the container.

28. The instrument of claim 1, wherein the entryway is biased toward the closed state.

29. The instrument of claim 1, wherein the entryway is configured for one-way passage of fragments into the container.

30. The instrument of claim 1, wherein:

the container is operatively coupled with an elongate member extending along the flexible elongate shaft, and longitudinal displacement of the elongate member with respect to the flexible elongate shaft selectively transitions the entryway between the open state and the closed state.

31. The instrument of claim 30, wherein:

the elongate member defines a drawstring extending along a circumference of the container at the entryway, and proximal displacement of the elongate member with respect to the flexible elongate shaft cinches the circumference to transition the entryway toward the closed state.

32. The instrument of claim 1, wherein:

the retaining mechanism comprises:

an auger blade extending along at least a portion of an auger lumen of the flexible elongate shaft;

an elongate auger member extending along the flexible elongate shaft; and a rotating actuator operatively coupled with the auger blade via the elongate auger member, and in use, the fragments are proximally displaced along the auger lumen in accordance with rotation of the auger blade upon activation of the rotating actuator.

33. The instrument of claim 1, further comprising a fragment gathering mechanism coupled with the flexible elongate shaft at the distal end, the fragment gathering mechanism configured to urge fragments toward the retaining mechanism.

34. The instrument of claim 33, wherein, in use, the fragment gathering mechanism extends distally beyond the retaining mechanism.

35. The instrument of claim 33, wherein:

the fragment gathering mechanism is selectively transitionable between a gathering configuration and a non-gathering configuration, proximal displacement of one or more fragments together with the fragment gathering mechanism is constrained when the fragment gathering mechanism is disposed in the gathering configuration, and relative displacement of the fragment gathering mechanism with respect to the fragments is allowed when the fragment gathering mechanism is disposed in the non-gathering configuration.

36. The instrument of claim 35, wherein:

the fragment gathering mechanism comprises a hook coupled with an elongate hook member extending along the flexible elongate shaft, and the hook is selectively transitionable between a curved shape defining the fragment gathering configuration and a straight shape defining the non-gathering configuration via manipulation of the elongate hook member at the proximal end of the flexible elongate shaft.

37. The instrument of claim 35, wherein:

the fragment gathering mechanism comprises two or more hooks coupled with two or more elongate hook members extending along the flexible elongate shaft, and the two or more hooks are transitionable between an expanded state defining the fragment gathering configuration and a contracted state defining the non-gathering configuration via manipulation of the two or more elongate hook members at the proximal end of the flexible elongate shaft.

38. The instrument of claim 35, wherein the fragment gathering mechanism comprises:

a central post coupled with a first elongate gathering member extending along the flexible elongate shaft;

a drill bit coupled with the central post at a distal end of the central post, the drill bit configured to form a hole extending through a fragment via rotation of the drill bit; and a rotating actuator coupled with the first elongate gathering member at the proximal end of the flexible elongate shaft.

39. The instrument of claim 38, wherein the fragment gathering mechanism further comprises:

two or more arms pivotably coupled with the central post, the two or more arms configured to extend radially outward from the central post defining the fragment gathering configuration, and to extend along the central post defining the non-gathering configuration; and a second elongate gathering member extending along the flexible elongate shaft, the second elongate gathering member operatively coupled with the two or more arms, wherein the two or more arms are transitionable between the fragment gathering configuration and the non-gathering configuration via longitudinal displacement of the second elongate gathering member with respect to the first elongate gathering member.

40. The instrument of claim 39, wherein in use:

the drill bit is rotated to form a hole through a fragment, the two or more arms are inserted through the hole in the fragment in the non-gathering configuration to thread the fragment onto the central post, and the two or more arms are transitioned to the fragment gathering configuration after insertion through the hole to prevent separation of the fragment from the central post.

41. The instrument of claim 38, wherein the fragment gathering mechanism further comprises:

an inflatable balloon coupled with a second elongate gathering member extending along the flexible elongate shaft;

a fluid lumen extending along the second elongate gathering member; and a fluid device coupled with the second elongate gathering member at the proximal end of the flexible elongate shaft, the fluid device in fluid communication with the inflatable balloon via the fluid lumen, wherein the inflatable balloon is selectively transitionable via manipulation of the fluid device between an inflated state defining the fragment gathering configuration, and a deflated state defining the non-gathering configuration.

42. The instrument of claim 41, wherein, in use:

the drill bit is rotated to form a hole extending through a fragment, the central post is threaded through the hole so that the inflatable balloon is disposed distal the fragment, and the inflatable balloon is transitioned to the inflated state to prevent separation of the fragment from the central post.

* * * * *